(12) United States Patent
Ferran et al.

(10) Patent No.: US 7,297,685 B2
(45) Date of Patent: Nov. 20, 2007

(54) USE OF PRO-APOPTOTIC FACTORS IN TREATMENT OF ATHEROSCLEROSIS

(75) Inventors: Christiane Ferran, West Roxbury, MA (US); Maria B. Arvelo, Quincy, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 353 days.

(21) Appl. No.: 10/461,200

(22) Filed: Jun. 13, 2003

(65) Prior Publication Data

US 2003/0207838 A1 Nov. 6, 2003

Related U.S. Application Data

(63) Continuation of application No. 09/765,519, filed on Jan. 19, 2001, now abandoned.

(60) Provisional application No. 60/177,535, filed on Jan. 21, 2000.

(51) Int. Cl.
*A61N 31/70* (2006.01)
*A61K 48/00* (2006.01)

(52) U.S. Cl. ...................... 514/44; 424/93.2

(58) Field of Classification Search ............... None
See application file for complete search history.

(56) References Cited

U.S. PATENT DOCUMENTS

| 5,459,251 A | 10/1995 | Tsujimoto et al. | 536/23.5 |
| 5,571,523 A | 11/1996 | Lee et al. | 424/423 |
| 5,776,905 A | 7/1998 | Gibbons et al. | 514/44 |
| 6,043,055 A | 3/2000 | Hsueh et al. | 435/69.1 |

FOREIGN PATENT DOCUMENTS

| EP | 0 670 369 A2 | 9/1995 |
| WO | WO 90/06997 | 6/1990 |
| WO | WO 92/07573 | 5/1992 |
| WO | WO 93/18794 | 9/1993 |
| WO | WO 94/10305 | 5/1994 |
| WO | WO 94/27426 | 12/1994 |
| WO | WO 95/00642 | 1/1995 |
| WO | WO 95/15084 | 6/1995 |
| WO | WO 97/30083 A1 | 8/1997 |

OTHER PUBLICATIONS

Ferran et al (Transplantation Proceedings 29: 879-880, 1997).*
VanBuskirk et al (Transplant Immunology 278(22): 1993-1999, 1997).*
Verma et al (Nature 389: 239-242, 1997).*
Anderson (Nature 392:25-30, 1998).*
Romano et al (Stem Cells 18: 19-39, 2000).*
Somia and Verma (Nature Reviews Genetics 1: 91-99, 2000).*
Rudinger (In Peptide Hormones J.A. Parsons, Ed. University Park Press, Baltimore, 1976, pp. 1, 6, and 7).*
Ngo et al (In The Protein Folding Problem and Tertiary Structure Prediction, K. Merz Jr. and S. Legrand, Eds. Birkhauser, Boston, 1994, pp. 433 and 492-495.).*
Miller et al. (FASEB J. 9: 190-199, 1995).*
Deonarain (Exp. Opin. Ther. Patents 8(1):53-69, 1998).*
Crystal (Science 270: 404-410, 1995).*
Pouton et al (Adv. Drug Del. Rev. 46: 187-203, 2001).*
Read et al (Adv. Gen. 53:19-46, 2005).*
Guo et al (Proc. Nat. Acad. Sci. USA 101(25):9205-9210, 2004).*
Anderson, "Human gene therapy," *Nature* 392:25-30 (1998).
Arvelo et al., "A novel function for A20 in smooth muscle cells: Inhibition of activation and proliferation. A means of protection from transplant-associated arteriosclerosis," *Transplant 98 Book of Abstracts* (Abstract) (1998).
Arvelo et al., "Combined expression of A20 in endothelial and smooth muscle cells serve an anti-inflammatory and anti-transplant arteriosclerosis potential: A means of achieving long-term xenograft survival," *The 5th Congress of the International Xenotransplantation Association* (Abstract) (1999).
Bach et al., "Accommodation of Vascularized Xenografts: Expression of "Protective Genes" by Donor Endothelial Cells in a Host Th2 Cytokine Environment," *Nature Medicine* 3:196-204 (1997).
Bach et al., "A20 gene therapy for transplantation and inflammatory conditions and means therefor," U.S. Appl. No. 09/576,464, filed May 23, 2000.
Bach et al., "Protective genes expressed in endothelial cells: a regulatory response to injury," *Immunology Today* 18:483-486 (1997).
Bach et al., "Delayed Xenograft Rejection," *Immunology Today* 17:379-383 (1996).
Bach et al., "Endothelial cell activation and thromboregulation during xenograft rejection," *Immunological Reviews* 141:5-30 (1994).
Badrichani et al., "Bcl-2 and Bcl-Xl Serve an Anti-Inflammatory Function in Endothelial Cells Through Inhibition of NF-kB," *The Journal of Clinical Investigation* 103:543-553 (1999).
Baldwin et al., "The NF-kB and IkB Proteins: New Discoveries and Insights," *Ann. Rev. Immunol.* 14:649-681 (1996).
Barinaga, "Life-death balance within the cell," *Science* 274:724 (1996).

(Continued)

*Primary Examiner*—Richard Schnizer
(74) *Attorney, Agent, or Firm*—Clark & Elbing LLP

(57) ABSTRACT

The present invention features a novel method of treating vascular disease that involves modifying smooth muscle cells to express a gene encoding a protein having both anti-inflammatory and pro-apoptotic activity. Preferably, the protein of the invention also has an anti-proliferative effect in smooth muscle cells. In general, the method is useful in preparing vascularized organs and vessels for transplant into a patient. Alternatively, the present invention can be applied to treat atherosclerotic lesions in damaged vessels.

17 Claims, 11 Drawing Sheets

OTHER PUBLICATIONS

Beg et al., "An essential role for NF-κB in preventing TNF-α-Induced cell death," *Science* 274:782-784 (1996).

Bellas et al., "Expression of a constitutive NF-kB-like activity is Essential for Proliferation of Cultured Bovine Vascular Smooth Muscle Cells," *J. Clin. Invest.* 96:2521-2527 (1995).

Björkerud et al., "Contrary Effects of Lightly and Strongly Oxidized LDL with Potent Promotion of Growth Verses Apoptosis on Arterial Smooth Muscle Cells, Moacrophages, and Fibroblasts," *Arterioscler. Thromb. Vasc. Biol.* 16:415-424 (1996).

Boise et al., "Bcl-x, bcl-2-related gene that functions as a dominant regulator of apoptotic cell death," *Cell* 74:597-608 (1993).

Bourcier et al., "The Nuclear Factor k-B Signaling Pathway Participates in Dysregulation of Vascular Smooth Muscle Cells in vitro and in Human Atherosclerosis," *J. Biol. Chem.* 272:15817-15824 (1997).

Brand et al., "Activated Transcription Factor Nuclear Factor-Kappa B is Present in the Atherosclerotic Lesion," *J. Clin. Invest.* 97:1715-1722 (1996).

Bustos and Platt, "Platlet-Endothelial Cell Interaction in a Xenograft Model," *Transplantation Proceedings* 29: 886 (1997).

Carrington et al., "Novel Responses to Transgenic Pig Endothelial Cells to Stimulation by Human Cytokines in Terms of H-Daf, E-Selectin and Major Histocompatibility Complex Class II Expression," *Transplantation Proceedings* 29: 887 (1997).

Choi et al., "The role of bcl-$x_L$ in CD40-mediated rescue from anti-μ-induced apoptosis in WEHI-231 B lymphoma cells," *Eur. J. Immunology* 25:1352-1357 (1995).

Clay et al., "Potential use of T cell receptor genes to modify hematopoietic stem cells for the gene therapy of cancer," *Pathology Oncology Research* 5:3-15 (1999).

Clemens et al., "Molecular basis for specific recognition of both RNA and DNA by a zinc finger protein," *Science* 260:530-533 (1993).

Collins, "Biology of disease. Endothelial nuclear factor-κB and the initiation of the atherosclerotic lesion," *Laboratory Investigation* 68(5):499-508 (1993).

Cooper et al., "A20 blocks endothelial cell activation through a NF-κB-dependent mechanism," *The Journal of Biological Chemistry* 271(30):18068-18073 (1996).

Cooper et al., "A20 Expression Inhibits Endothelial Activation," *Transplantation Proceedings* 29: 881 (1997).

Craig, "The BCL-2 gene family," *Seminars in Cancer Research* 6:35-43 (1995).

Crook et al., "An apoptosis-inhibiting baculovirus gene with a zinc finger-like motif," *Journal of Virology* 67:2168-2174 (1993).

Crystal, "Transfer of genes to humans: early lessons and obstacles to success," *Science* 270:404-410 (1995).

de Martin et al., "Cytokine-inducible expression in endothelial cells of an IκBα-like gene is regulated by NfκB," *The EMBO Journal* 12(7):2773-2779 (1993).

Dixit et al., "Tumor nacrosis factor-α induction of novel gene products in human endothelial cells including a macrophage-specific chemotaxin," *J. Biol. Chem.* 265:2973-2978 (1990).

Dixit et al., "The antimitogenic action of tumor necrosis factor is associated with increased ap-1/c-jun proto-ocogene transcription," *J. Biol. Chem.* 264:16905-16909 (1990).

Evans et al., "Zinc Fingers: Gilt by association," *Cell* 52:1-3 (1988).

Ferran et al., "Inhibition of NF-kB by Pyrrolidine Dithiocarbamate Blocks Endothelial Cell Activation," *Biochemical and Biophysical Research Communication* 214:212-223 (1995).

Ferran et al., "A20 inhibits NF-κB activation in endothelial cells without sensitizing to tumor necrosis factor-mediated apoptosis," *Blood* 91:2249-2258 (1998).

Ferran et al., "Adenovirus-mediated gene transfer of A20 renders endothelial cells resistant to activation: a means of evaluating the role of endothelial cell activation in xenograft rejection," *Transplantation Proceedings* 29:879-880 (1997).

Fox et al., "Antisense Inhibition of Basic fibroblast growth factor induces apoptosis in vascular snooth muscle cells," *J. Biol. Chem.* 271:12578-12584 (1996).

Fryer et al., "Inhibition of Human Serum Mediated Lysis of Porcine Endothelial Cells Using a Novel Peptide Which Blocks C1Q Binding to Xenoantibody," *Transplantation Proceedings* 29: 883 (1997).

Genebank Accession No. A35797 (1999).

Genebank Accession No. B47537 (1999).

Geng et al., "Apoptosis of vascular smooth muscle cells induced by in Viro stimulation with interferon-γ, tumor necrosis factor-α, and interleukin-1β," *Arterioscler. Thromb. Vasc. Biol.* 16:19-27 (1996).

Gossen et al., "Efficacy of tetracycline-controlled gene expression is influenced by cell type: commentary," *Biotechniques* 19:213-216 (1995).

Gottschalk et al., "Identification of immunosuppressant-induced apoptosis in a murine B-cell line and its prevention by bcl-x but not bcl-2," *Proc. Natl. Acad. Sci. USA* 91:7350-7354 (1994).

Grey et al., "Adenovirus-mediated gene transfer of A20 in murine islets inhibits iNOS induction and protects from apoptosis: A novel candidate for genetic manipulation of islet grafts," *Transplant 98 Book of Abstracts* (Abstract) (1998).

Grey et al., "Protective effect of A20 in islets: A means of achieving successful xenotransplantation," *The 5th Congress of the Cao International Xenotransplantation Association* (Abstract) (1999).

Grilli et al., "NF-κB and Rel:Participants in a Multiform Transcriptional Regulatory System," *International Review of Cytology* 13:1-61 (1993).

Grimm et al., "Bcl-2 down-regulates the activity of transcription factor NF-κB induced upon apoptosis," *The Journal of Cell Biology* 134(1):13-23 (1996).

Guo et al., "Overexpression of Bax enhances antitumor activity of chemotherapeutic agents in human head and neck squamous cell carcinoma," 2000:162761 *Clinical Cancer Research* 6:718-724 (2000).

Guzman et al., "Efficient and selective adenovirus-mediated gene transfer into vascular neointima," *Circulation* 88(6):2838-2848 (1993).

Hammer et al., "Spontaneous inflammatory disease in transgenic rats expressing HLA-B27 and human $β_2$m: an animal model of HLA-B27-associated human disorders," *Cell* 63:1099-1112 (1990).

Heyninck et al., "The cytokine-inducible zinc finger protein A20 inhibits IL-1-induced NF-κB activation at the level of TRAF6," *FEBS Lett.* 442:147-150 (1999).

Heyninck et al., "The zinc finger protein A20 inhibits TNF-induced NF-κB-dependent gene extpression by interfering with an RIP- or TRAF2-mediated transactivation signal and directly binds to a novel NF-κB-inhibiting protein ABIN," *J. Cell Biol.* 145:1471-1482 (1999).

Isner et al., "Apoptosis in human atherosclerosis and restenosis," *Circulation* 91(11): 2703-2711 (1995).

Ivanov et al., "Pleiotropic effects of Bcl-2 on transcription factors in T cells: potential role of NF-κB p50-p50 for the anti-apoptotic function of Bcl-2," *International Immunology* 7(11):1709-1720 (1995).

Iwahashi et al., "Cytokine-induced apoptotic cell death in a mouse pancreatic beta-cell line: inhibition by Bcl-2," *Diabetologie* 39L:530-536 (1996).

Jäättelä et al., "A20 zinc finger protein inhibits TNF and IL-1 signalling," *J. Immunology* 156(3):1166-1173 (1996).

Jäättela et al., "Bcl-x and Bcl-2 Inhibit TNF and Fas-Induced Apoptosis and Activation of Phospholipase A2 in Breast Carcinoma Cells ,"*Oncogene* 10:2297-2305, (1995).

Karsan et al., "Endothelial cell death induced by tumor necrosis factor-β is inhibited by the Bcl-2 family member, A1," *The Journal of Biological Chemistry* 271(44):27201-27204 (1996).

Kato et al., "Overexpression of p21Waf-1 in vascular smooth muscle cells: regulation of proliferation, differentiation, and cell size," *Experimental and Molecular Pathology* 66:39-52 (1999).

Kim et al., "Bid-induced cytochrome c release is mediated by a pathway independent of mitochondrial permeability transition pore and bax," *J. Biol. Chem.* 275:39474-39481 (2000).

Kondo et al., "bcl-2 gene prevents apoptosis of basic fibroblast growth factor-deprived murine aortic endothelial cells," *Expl. Cell Res.* 213:438-432 (1994).

Krikos et al., "Transcriptional activation of the tumor necrosis factor α-inducible zinc finger protein, A20, is mediated by κB elements," *J. Biol. Chem.* 267(25):17971-17976 (1992).

Laherty et al., "The epstein-barr virus LMP1 gene product induces A20 zinc finger protein expression by activating nuclear factor κB," *J. Biol. Chem.* 267:24157-24160 (1992).

Laherty et al., "Human T cell leukemia virus type I tax and phorbol 12-myristate 13-acetate induce expression of the A20 zinc finger protein by distinct mechanisms involving nuclear factor κB," *The Journal of Biological Chemistry* 268(7):5032-5039 (1993).

Lawson et al., "The Evaluation of Thrombomodulin Activity in Porcine to Human Xenotransplantation," *Transplantation Proceedings* 29: 884 (1997).

Lin et al., "Thiol agents and Bcl-2 identity an alphavirus-induced apoptotic pathway that requires activation of the transcription factor NF-kappa B," *The Journal of Cell Biology* 131(5):1149-1161 (1995).

Lin et al., "Characterization of A1, a novel hemopoietic-specific early-response gene with sequence similarity to Bcl-2," *The Journal of Immunology* 151:1979-1988 (1993).

Mann et al., "Genetic engineering of vein grafts resistant to atherosclerosis," *Proc. Natl. Acad. Sci. USA* 92:4502-4506 (1995).

Martinou et al., "Overexpression of BCL-2 in transgenic mice protects neurons from naturally occurring cell death and experimental ischemia," *Neuron* 13:1017-1030 (1994).

Miyatake et al., "Survival of Accomodated Cardiac Xenografts Upon Retransplantation into Cyclosporine-Treated Recipients," *Transplantation* 65:1563-1569 (1998).

Natoli et al., "Nuclear factor κB-independent cytoprotective pathways originating at tumor necrosis factor receptor-associated factor 2," *J. Biol. Chem.* 273:31262-31272 (1998).

Oltval et al., "Bcl-2 heterodimerizes in vivo with a conserved homolog, bax that accelerates programed cell death," *Cell* 74:609-619 (1993).

Opipari et al., "The A20 cDNA induced by tumor necrosis factor a encodes a novel type of zinc finger protein," *The Journal of Biological Chemistry* 265(25):14705-14708 (1990).

Opipari et al., "The A20 zinc finger protein protects cells from tumor necrosis factor cytotoxicity," *The Journal of Biological Chemistry* 267(18):12424-12427 (1992).

"Report and Recommendations of the Panel to Assess the NIH Investment in Research on Gene Therapy," Orkin and Motulsky, co-chairs. The National Institutes of Health (1995).

Pollman et al., "Vasoactive substances regulate vascular smooth muscle cell apoptosis," *Circ. Res.* 79:748-756 (1996).

Read et al., "NF-kB and IkBo: An inducible regulatory system in endothelial activation," *J. Experimental Medicine* 179:503-512 (1994).

Sarma et al., "Activation of the B-cell surface receptor CD40 induces A20, a novel zinc finger protein that inhibits apoptosis," *The Journal of Biological Chemistry* 270(21):12343-12346 (1995).

Sata et al., "Fas ligand gene transfer to the vessel wall inhibits neointima formation and overrides the adenovirus-mediated T cell response," *Proc. Natl. Acad. Sci. USA* 95:1213-1217 (1998).

Selzman et al., "The NFκB inhibitory peptide, IκBα, prevents human vascular smooth muscle proliferation," *Ann. Thorac. Surg.* 67:1227-1232 (1999).

Shaw et al., "Knotting of a DNA chain during ring closure," *Science* 260:533-536 (1993).

Stroka et al., "Expression of a Negative Dominant Mutant of a Human P55 Tumor Necrosis Factor-Receptor Inhibits TNF and Monocyte-Induced Activation in Porcine Aortic Endothelial Cells," *Transplantation Proceedings* 29: 882 (1997).

Tewari et al., "Lymphoid expression and regulation of A20, an inhibitor of programmed cell death," *J. Immunol.* 154:1699-1706 (1995).

Tsai et al., "Induction of apoptosis by pyrrolidinedithiocarbamate and N-acetylcysteine in vascular smooth muscle cells," *J. Biol. Chem.* 271:3667-3670 (1996).

Tucker et al., "Endothelial Cells from Human Decay Acceleration Factor Transgenic Pigs are Protected Against Complement Mediated Tissue Factor Expression in Vitro," *Transplantation Proceedings* 29: 888 (1997).

Vandenabeele et al., "Functional requirement of the two TNF receptors for induction of apoptosis in pc60 cells and the role of mitochondria in the TNF-induced cytotoxicity" *Circulatory Shock* 44:196-200 (1994).

Verma et al., "Gene therapy—promises, problems and prospects" *Nature* 389:239-242 (1997).

Vincenz et al., "14-3-3 proteins associate with A20 in an isoform-specific manner and function both as chaperone and adapter molecules," *J. Biol. Chem.* 271:20029-20034 (1996).

Wang et al., "TNF- and cancer therapy-induced apoptosis: potentiation by inhibition of NF-κB," *Science* 274:784-787 (1996).

White et al., "Life, death, and the pursuit of apoptosis," *Genes & Development* 10:1-15 (1996).

Wrighton et al., "High-level expression of functional human thrombomodulin in cultured porcine aortic endothelial cells," *Transplantation Proceedings* 27(1):288-289 (1995).

Wu et al., "Inhibition of NF-κB/Rel induces apoptosis of murine B cells," *The EMBO Journal* 15(17):4682-4690 (1996).

Yang et al., "Molecular thanatopsis: A discourse on the BCL2 family and cell death," *Blood* 88(2):386-401 (1996).

Yang et al., "MCL-1, a member of the BCL-2 family, is induced rapidly in response to signals for cell differentiation or death, but not to signals for cell proliferation," *Journal of Cellular Physiology* 166:523-536 (1996).

Yeong Song et al., "The Tumor Necrosis Factor-Inducible Zinc Finger Protein A20 Interacts with TRAF1/TRAF2 and Inhibits NF-κB Activation," *Proc. Nat. Acad. Sci. USA* 93:6721-6725 (1996).

* cited by examiner

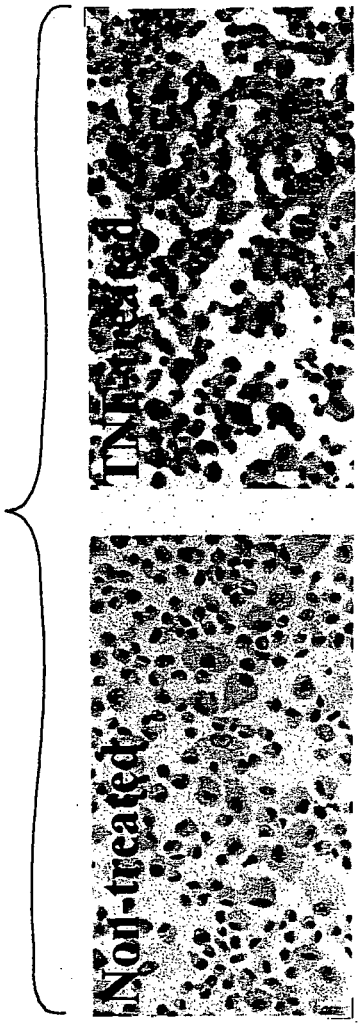
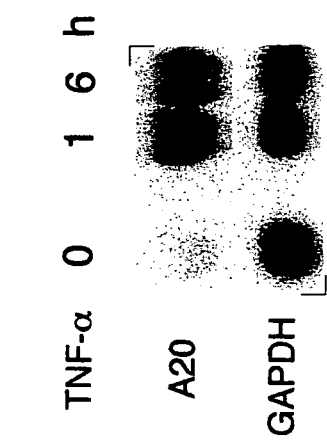
FIG. 1B
FIG. 1A

USE OF PRO-APOPTOTIC FACTORS IN TREATMENT OF ATHEROSCLEROSIS

CROSS REFERENCE TO RELATED APPLICATIONS

The present application is a continuation of U.S. patent application Ser. No. 09/765,519, filed Jan. 19, 2001, abandoned, which claims benefit to provisional application 60/177,535 filed Jan. 21, 2000, the entire contents of which are incorporated herein by reference.

STATEMENT AS TO FEDERALLY SPONSORED RESEARCH

The present research was supported by a grant from the National Institutes of Health (NIH) (Grant R01 Number HL57791-02).

FIELD OF THE INVENTION

The present invention relates to the field of vascular disease.

BACKGROUND OF THE INVENTION

Vascular disease is the most common cause of morbidity and mortality in the western world, surpassing any other single degenerative disease. The fundamental pathology of vascular disease is an abnormal accumulation of cells within the subintimal space below the surface of the endothelial cell lining, resulting in a decrease in lumen size and tissue perfusion. This accumulation is due to the proliferation and/or migration of smooth muscle cells, and/or inflammatory cells into the intimal layer of a vessel, resulting in restricted blood flow through that vessel, i.e. neointimal occlusive lesions.

Current efforts aimed at preventing and treating vascular disease are directed at developing improved lipid-lowering agents (e.g., for treatment of atherosclerosis) and immunosuppressive regimens. For example, lipid lowering agents are currently used in the treatment of atherosclerosis. Alternatively, immunosuppressive regimes are used in allotransplantation for prevention of transplant-associated vasculopathy (TAV), also referred to as transplant arteriosclerosis. TAV is closely related to atherosclerosis and remains the major barrier to successful transplantation (Brooks-Wilson et al., *Nature Genetics*, (1999) 22:327-335; Kirk et al., *Nature Medicine* (1999) pages 686-693; Hancock et al., *Nature Medicine*, (1998) 4:1392-1396). Alternatively, surgical strategies have been developed that are aimed at bypassing the obstruction with venous conduits, or stretching the vessel to create a larger lumen by performing balloon angioplasty.

Despite the substantial benefit attributable to the use of current cholesterol lowering and immunosuppressive drug therapies, these treatments do not achieve an acute reduction in vascular lesion size. Furthermore, bypass surgery may accelerate progressive lesion stenosis, and interventions such as balloon angioplasty often result in the development of restenosis. There exists the need of a strategy for preventing and treating vascular disease.

The role of the protein A20 has been studied extensively in endothelial cells and suggests that A20 plays an anti-apoptotic role in response to inflammatory stimulus.

SUMMARY OF THE INVENTION

The present invention is based on the finding that A20 is a pro-apoptotic factor in smooth muscle cells, a finding which would not have been predicted based on the anti-apoptotic role previously established for A20 in endothelial cells. The present invention thus provides therapeutic strategies for up-regulating pro-apoptotic factors in smooth muscle cells for prevention and treatment of vascular disease.

Specifically, the present invention provides a method of treating vascular disease by (1) modifying mammalian smooth muscle cells so that they exhibit increased anti-inflammatory and pro-apoptotic activity, and (2) transplanting the smooth muscle cells into a transplant candidate or a patient diagnosed with a vascular disease (e.g., atherosclerosis, transplant-associated vasculopathy, or chronic rejection). Preferably, the smooth muscle cells are selectively treated. For example, the present invention is useful in the treatment and prevention of atherosclerosis and transplant-associated vasculopathy (TAV). The increase in anti-inflammatory and pro-apoptotic activity is accomplished by inserting into the smooth muscle cell, or a progenitor thereof, DNA encoding A20 capable of decreasing inflammation and increasing apoptosis of the smooth muscle cell. Preferably the A20 protein employed by the methods of the invention also achieves an anti-proliferative effect in the smooth muscle cell. A key feature of the invention is that the methods include introduction of nucleic acid to a tissue or organ having smooth muscle cells, such as a vessel, a heart, a kidney or a liver into smooth muscle cells.

In a related aspect, the method of the present invention can be applied to prevent TAV in a patient at risk for developing TAV. This method involves modifying a mammalian smooth muscle cell by inserting into the smooth muscle cell DNA encoding a protein capable of decreasing inflammation and increasing apoptosis of the smooth muscle cell and transplanting the smooth muscle cell (or tissue or organ having a smooth muscle cell) into the patient. A patient classified as a patient at risk for developing TAV would be, for example, a patient receiving an organ or vessel transplant.

Where the method of the invention is applied to the prevention or treatment of vascular disease, the anti-inflammatory/pro-apoptotic protein is preferably the A20 protein. The present invention is based on the discovery that the A20 protein, previously thought to be an anti-apoptotic factor, has pro-apoptotic activity in smooth muscle cells. Included in certain aspects of the invention is the use of mutants and derivatives of the A20 protein that may have increased activity or expression in smooth muscle cells.

In another related aspect, the invention provides a method of treating atherosclerosis, or preventing TAV by transplanting donor smooth muscle cells, or graftable tissues or organs having smooth muscle cells into a mammalian recipient diagnosed with atherosclerosis or at risk for developing TAV. The first step requires modifying the donor smooth muscle cells, or progenitor cells thereof, by inserting therein nucleic acid encoding the A20 protein. The second step requires transplanting the resultant modified donor smooth muscle cells, or tissue, or organ comprising the cells into the recipient and expressing in the cells the A20 protein, thereby substantially promoting apoptosis. Preferably, smooth muscle cells modified by this procedure are capable of substantially inhibiting inflammation in the presence of a cellular activating stimulus (e.g., TNF).

The present invention also provides a method of preparing a vascularized organ or vessel for transplantation into a patient by obtaining an organ or vessel for transplant and perfusing the organ with nucleic acid encoding the A20 protein. A variety of vectors are available in the art for gene transfer. Particularly preferred vectors are the adenovirus vector and the lentivirus vector. In a preferred embodiment, the organ or vessel is perfused with a gene transfer vector and an immunoregulatory factor (e.g., a cytokine). Alternatively, a therapeutic agent may be perfused into the organ or vessel to enhance the expression of A20.

Organ and vessel transfer procedures can be most effectively applied to patients that have suffered ischemia, reperfusion injury, mechanical injury, immunologic injury, pharmacologic injury, or coronary trauma. Alternatively, methods of organ and vessel transfer can be applied to a patient who has undergone undergone balloon angioplasty. However, the most preferred application of the organ or vessel transfer procedure of the present invention is in the treatment of patients diagnosed with atherosclerosis. Preferably, the organ or vessel being prepared is a vascularized organ transplant or a vascular graft.

The present invention also relates to a mammalian smooth muscle cell that is modified to express the A20 protein. Expression of the A20 protein imparts on the smooth muscle cell an anti-inflammatory/pro-apoptotic effect in the presence of a cellular activating stimulus. The modified smooth muscle cell thereby exhibits increased apoptosis, relative to an untreated smooth muscle cell. In preferred embodiments, the A20 protein also blocks smooth muscle cell proliferation. Similarly, the present invention also relates to a donor smooth muscle cell, or a tissue or organ having a smooth muscle cell, for transplantation into a recipient species, wherein the cell is modified to express A20. Alternatively, a therapeutic agent may applied to the cell to enhance the expression of A20.

In another related aspect, the invention provides an organ or vessel from a non-human transgenic or somatic recombinant mammal comprising DNA encoding a pro-apoptotic protein of a different species. The non-human transgenic or recombinant mammal thus acts as a stable source of transplant tissue. Preferably, the non-human animal is porcine and the pro-apoptotic factor is human.

The present invention also provides a method of identifying compounds that substantially promote apoptosis and substantially inhibit growth or proliferation in smooth muscle cells. The method requires exposing smooth muscle cells to a test compound and assaying the smooth muscle cells for increased apoptosis and reduced growth or proliferation. A variety of methods are available for assaying increased apoptosis and reduced growth or proliferation. Primarily, assays that measure A20 biological activity in smooth muscle cells (i.e., the ability to promote apoptosis and inhibit proliferation) will be used to assess the effect of a compound. Alternatively, these assays represent methods of detecting binding of a compound to a pro-apoptotic protein of interest (i.e., A20). Particularly preferred compounds include compounds that enhance A20 biological activity or increase the level of A20 in a smooth muscle cell.

In another preferred embodiment, the present invention also provides a method of treating a patient having a vascularized organ transplant, a vessel transplant, or vascular disease by enhancing A20 biological activity. Therapeutic agents, such as the compounds identified as described above, that enhance A20 biological activity, can be used to treat patients having vascularized organ transplants, vessel transplants, or vascular diseases. Such compounds can also be applied to the prevention of vascular disease in a patient. Such compounds are preferably in the form of a therapeutic agent, e.g., a cytokine, Fas, or a drug. Alternatively, a mutant A20 gene might be employed that encodes an A20 protein that exhibits increased A20 biological activity.

The present invention also relates to a method of promoting apoptosis in smooth muscle cells in a patient, by increasing the level of A20 in the smooth muscle cells. One mechanism of achieving this goal is to modify smooth muscle cells to express A20. Another mechanism by which to achieve increased A20 expression in a smooth muscle cell is to employ a mutant of the A20 gene encoding a protein that is expressed at a higher level in A20 cells. Yet another mechanism by which the level of A20 protein can be increased in a smooth muscle cell is by administration of a therapeutic agent to the smooth muscle cell, (e.g., a cytokine, a transcription factor, Fas, or a drug). Preferably, the method is used to treat a patient with a vascularized organ transplant, a vessel transplant or vascular disease (e.g., TAV, or atherosclerosis).

Definitions

"Vascular disease," is used herein to refer to atherosclerosis, transplant-associated vasculopathy, chronic rejection, stenosis (e.g., vein graft stenosis or peri-anastomatic prosthetic graft stenosis), restenosis (e.g., restenosis after angioplasty or stent placement, and the like), human atheroma, septic shock, and vasculitis. Vascular disease also refers to vascular conditions that develop after a surgical treatments, such as, venous bypass surgery, balloon angioplasty, post-angioplasty of atherosclerotic plaques of both coronary and peripheral arteries, and allo- and xenograft rejection. Alternatively, vascular disease is used to refer to the disease of a patient that has suffered ischemia, reperfusion injury, mechanical injury, immunologic injury, pharmacologic injury of a vessel, or coronary trauma. In yet another embodiment, the patient has undergone balloon angioplasty.

"A20" refers to a natural mammalian A20 gene, including the cDNA or protein thereof. A20 also include derivatives having variations in the cDNA (SEQ ID NO:1) or amino acid (SEQ ID NO:2) sequence. Included in the definition of A20 are derivatives of the A20 protein having conserved amino acid substitutions. In addition, A20 includes mutants having alterations in one or more amino acids that either maintain or increase the activity of A20. The A20 gene or protein employed in the invention may, for example, be porcine, bovine, or primate (e.g., a human), depending on the nature of the cells to be modified and the intended recipient species for transplantation.

By "A20 gene" is meant a gene encoding a polypeptide having A20 pro-apoptotic/anti-inflammatory activity in smooth muscle cells or other biological activities described herein. An A20 gene is a gene encoding an A20 polypeptide having about 60% or greater, more preferably 70% or greater amino acid sequence identity to the A20 amino acid sequence of SEQ ID NO:2, or a portion thereof. For example, the gene may encode human or murine A20 polypeptide. An A20 gene may also be defined as encoding a polypeptide with at least 50% of the activity of the A20 polypeptides described below. Preferably, the A20 gene is a human or murine A20 gene. In a further aspect, the A20 gene of the invention is at least 70%, and more preferably at least 80%, or at least 90% homologous to SEQ ID NO:1.

A protein or polypeptide "having A20 activity" or "A20 active protein" refers to a protein which is able to block or suppress nuclear factor κB (NF-κB) activation, and which is at least 70%, preferably at least 80%, and more preferably at least 90% (most preferably at least 95%) homologous to the protein sequence of a natural mammalian A20 protein (e.g., human) (SEQ ID NO:2) (see, Dixit et al., *J. Biol. Chem.*, (1990) 265:2973, and WO 05/0062, which are hereby incorporated by reference). Preferably, by blocking is meant at least 50% inhibition of IκB degradation that occurs after TNF stimulation, but blocking can also mean a 50% or greater inhibition of NFκB binding to κB elements on the DNA, or a 50% or greater decrease in the up-regulation of mRNA seen for NFκB-regulated genes following TNF treatment, such genes include, for example, ICAM-1 and MCP-1.

By "therapeutic gene" is meant a DNA that achieves an anti-proliferative, pro-apoptotic effect in smooth muscle cells. In addition, the therapeutic gene may also have the effect of decreasing inflammation, (e.g., by inhibiting NF-κB activation in a smooth muscle cell).

"Inflammation" refers to a cellular response to TNF that constitutes in part activation of NF-κB. An "anti-inflammatory" is a permeable factor (protein, peptide, or chemical agent (i.e., a drug)) that suppresses, inhibits or blocks the cellular response to TNF and NF-κB activation.

"Host" or "recipient" refers to the body of the patient into whom donor biological material is grafted. Preferably, the host is an animal which is of interest for experimental investigations, providing a model for treatment of human disease. More preferably, the host is a mammal or patient, and may be any mammalian species. For example, the mammalian host may be a rodent (e.g., including mice, rats and hamsters), or another mammal (e.g., rabbits, equines, bovines, canines, felines, etc.). Such mammals are of interest for the study of experimentally induced vascular lesions. A particularly preferred host is a primate. A most preferred mammalian host is a human.

A "patient at risk" for developing TAV may include all patients receiving allo- or xenogeneic tissue or organ transplants.

A "vascularized organ transplant," according to the present invention, includes any organ having vasculature and containing smooth muscle cells. For example, the heart, liver, and kidney are vascularized organs that can be used for transplant according to the present invention. "Vascularized organ transplant," as used herein, refers to any organ that may be used in a transplant procedure to replace a like organ that has suffered end-stage organ failure.

"Graft," "transplant", or "implant" are used interchangeably to refer to biological material derived from a donor for transplantation into a recipient, and to the act of placing such biological material in the recipient.

"Allogeneic" refers to the donor and recipient being of the same species (also, allograft). As a subset thereof, "syngeneic" refers to the condition wherein donor and recipient are genetically identical. "Autologous" refers to donor and recipient being the same individual. "Xenogeneic" (and "xenograft") refer to the condition where the graft donor and recipient are of different species.

By "constitutive" when used in reference to a promoter is meant substantially continuous transcription of the gene and expression of the protein over the life of the cell.

By "regulable" when used in reference to a promoter is meant that the transcription of the gene and expression of the protein is related to the presence, or absence, of a given substance. An embodiment of "regulable" expression includes "inducible" expression, i.e. whereby transcription (and thus protein expression) occurs on demand in response to a stimulus. The stimulus may comprise activating stimuli or a predetermined external stimulus. The activating stimuli may be any of the stimuli which give rise to changes in the endothelium or smooth muscle cells of donor tissue or organs which contribute to vascular disease. The predetermined external stimulus may be the presence of a drug, cytokine, or other agent. An example of a drug stimulus is tetracycline, which has the ability to activate the tetracycline responsive promoter. Alternatively, the activating stimuli may be TNF mediated NF-κB activation.

"Candidate compound," "test compound," "agent," or "therapeutic agent" as used herein include any molecule or permeable factor, e.g., a protein or pharmaceutical, i.e., a drug, with the capability of substantially promoting apoptosis and substantially inhibiting smooth muscle cell growth or proliferation.

By "A20 biological activity" as used herein, is meant, the ability of A20 to decrease inflammation and increase apoptosis in smooth muscle cells. Preferably, A20 biological activity also includes the ability to decrease proliferation of smooth muscle cells. A variety of assays are described herein (see, Examples) that measure A20 biological activity.

By "enhanced biological activity" as used herein in reference to the A20 protein, is meant, that the pro-apoptotic/anti-proliferative activity of the A20 protein has been increased above that of the wild-type A20 protein.

By "increased level" as used herein, is meant that the A20 protein is present in a greater quantity or has greater biological activity in a modified smooth muscle cell compared to the level of A20 protein in an unmodified wild-type smooth muscle cell.

BRIEF DESCRIPTION OF THE DRAWING

FIG. 1 is a photograph of a Western blot depicting A20 expression induction by TNF (panel A) and a photograph of immunohistochemical analysis of A20 expression in smooth muscle cells after TNF treatment (panel B).

DESCRIPTION OF THE PREFERRED EMBODIMENTS

Figure 2A:
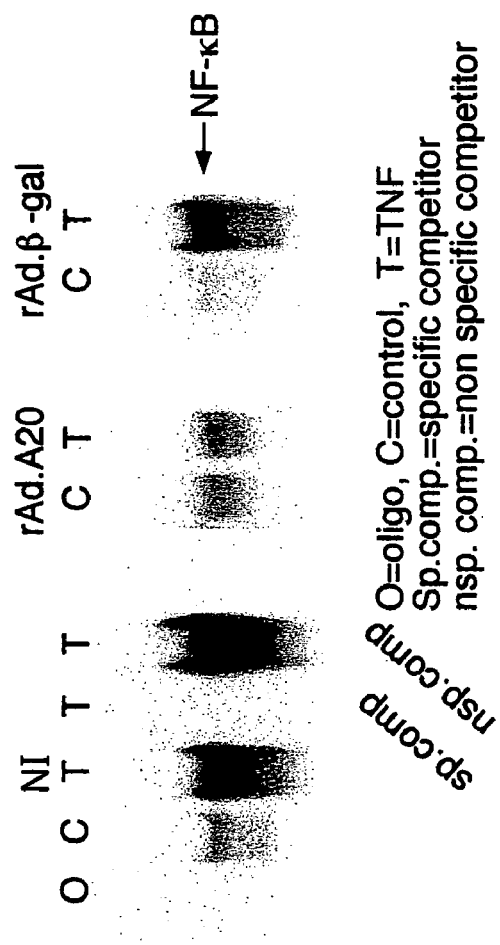
FIG. 2 is a photograph of an electrophoretic mobility shift assay (EMSA) depicting inhibition of NF-κB binding to DNA upon A20 expression (panel A) and a photograph of a Western blot depicting inhibition of IκBA degradation in the presence of A20 (panel B).

The present invention provides an alternative approach to inhibiting atherosclerosis through modifying cells in the vessel wall, particularly smooth muscle cells, that appear to be involved in the development of lesions associated with vascular disease, particularly atherosclerosis and TAV. This approach may offer the advantage of protecting against atherosclerosis and TAV regardless of the factors responsible for their initiation. According to the present invention, a "therapeutic gene" encoding and expressing a therapeutic protein achieves an anti-inflammatory, pro-apoptotic effect in smooth muscle cells (SMC). Preferably, the therapeutic gene also achieves an anti-proliferative effect in smooth muscle cells. Most preferably, the therapeutic gene also achieves an anti-inflammatory effect in endothelial cells (EC).

Atherosclerosis and Transplant Associated Vasculopathy

Atherosclerosis may be viewed as a chronic inflammatory response to high concentrations of oxidized LDL (Steinberg, *Nutrition and Biotechnology in Heart Disease and Cancer*, 1995 pages 39-48; Ross, *N. Engl. J. Med.*, (1986) 314:488-500). This response consists of a series of cellular and biochemical events. The present invention is based on the concept that mediators released by cells in the lesion may contribute to the development of atherosclerosis.

Although the initiating factors of atherosclerosis and TAV are different, fundamental pathological features are similar and relate to the dysregulation of the two major cell types of the vessel wall: SMC and EC. SMC contribute to the atherosclerotic lesion by essentially three mechanisms: (i) promotion of inflammation, (ii) aberrant SMC proliferation and migration within the neointima, and (iii) dysregulated SMC apoptosis (Ross, supra, Pomerantz et al., *Nutrition and Biotechnology in Heart Disease and Cancer* 1995 page 4964; Rekhter et al., *Am. J. Pathol.* (1995) 147:668-667; Bennett, *Cardiovasc. Res.* (1999) 41:361-368; Pollman et al., *Nat. Med.* (1998) 4:222-227; Rekhter, *Cardio. Res.* (1999) 141:376-384; Koyama et al., *Cell.* (1996) 87:1069-1078). EC cells contribute to the development of the atherosclerotic lesion by acquiring an inflammatory phenotype that promotes leukocyte infiltration, macrophage infiltration, coagulation and platelet aggregation. EC cell activation further leads to thrombosis and ischemia, foam cell development, matrix deposition, as well as promotion of SMC migration and proliferation in the neointima (Cotran et al., *J. Am. Soc. Nephrol.* (1990) 1:225-235; Gimbrone, *American Journal of Cardiology* (1995) 75:67B-70B).

Transplant-associated vasculopathy (TAV) is the main feature of chronic allograft rejection. TAV is a form of accelerated atherosclerosis resulting from a chronic inflammatory process initiated by the immune response to the allograft (Tullius et al., *Transplantation* (1995) 59:2126-2128; Ardehali et al., *Circulation* (1995) 92:450-456). Pathologically, with the exception of foam cell development, the lesions of TAV are quite similar to those of the atherosclerotic plaque. The present invention provides insight into the pathogenesis of these related diseases and the regulatory processes which maintain the structure and homeostatic functions of a healthy vessel. Through this understanding, a strategy for protecting vessels from atherosclerosis and TAV is proposed.

A20

A20 is a zinc finger protein originally identified as a tumor necrosis factor (TNF)-inducible gene in human umbilical vein endothelial cells (HUVEC) (Opipari et al., *J. Biol. Chem.* (1990) 265:14705-14708). A20 is expressed in a variety of cell types in response to a number of stimuli such as interleukin (IL)-1 in HUVEC, CD40 cross-linking in B cells, phorbol 12-myristate 13-acetate (PMA) or HTLVI Tax protein in Jurkat T cells, Epstein Barr Virus latent membrane protein-1 and lipopolysaccharide (LPS) (Tewari et al., *J. Immunol.* (1995) 154:1699-1706; Laherty et al., *J. Biol. Chem.* (1992) 267:24157-24160; Sarma et al., *J. Biol. Chem.* (1995) 270:12343-12346). It has been established that expression of A20 in various cell types, including EC cells, confers resistance to TNF-mediated apoptosis (Tewari et al., supra; Opipari et al., *J. Biol. Chem.* (1992) 267:12424-12427; Ferran et al., *Blood* (1998) 91:2249-2258). Thus, A20 has been thought of as an anti-apoptotic factor.

Morphologically, apoptosis is characterized by loss of contact with neighboring cells, concentration of cytoplasm, endonuclease activity-associated chromatin condensation, pyknosis, and segmentation of the nucleus. Disappearance of microvilli from the cell surface and vesicle formation on the cell surface (membrane blebbing) are also observed. The remaining fragments of apoptotic body cells are phagocytosed by neighboring cells (see, Duvall, E. and Wyllie, A. H., *Immunology Today* (1986) 7(4):115-119).

Traditionally, apoptotic cell death is considered to be of fundamental importance in inflammation, embryogenesis, and lymphocyte selection. Avoidance of cell activation and apoptotic cell death accompanying inflammation, particularly in connection with organ transplantation, has become a major goal for researchers in the art. In endothelial cells, graft injury and loss occurring in connection with graft preservation techniques and accompanying graft rejection exemplify the need for prevention of such a process. However, the present invention is based on the premise that promotion of apoptosis may actually be desirable for graft preservation and prevention of atherosclerosis and TAV in certain cell types, including smooth muscle cells.

The cDNA and deduced amino acid sequences of the human A20 gene obtained from HUVEC were published by Opipari et al. (*J. Biol. Chem.* (1992) 267:12424-12427), as indicated herein above. At the protein level, the deduced sequence of 790 amino acids contains within its carboxyl terminal half 7 $Cys_2/Cys_2$ zinc finger repeats; six with the configuration $Cys-X_4-Cys-X_{11}-Cys-X_2-Cys$ (SEQ ID NO: 5) and one with the configuration $Cys-X_2-Cys-X_{11}-Cys-X_2-Cys$ (SEQ ID NO: 6), wherein X is any amino acid and the subscripts represent numbers of amino acids between each of the indicated cysteines. The zinc finger repeat region is important for activity of A20 in endothelial and other cell types. A novel finger loop domain composed of 11 amino acid residues has also been identified (see Opipari et al., supra). In one embodiment of this invention, the protein having A20 activity comprises amino acid residues 386-790 of SEQ ID NO:2, comprising the zinc finger region of the native protein sequence, or a region at least 80% homologous to the residues. Another suitable truncated form of the native human protein consists essentially of residues 373-790 of SEQ ID NO:2. A person skilled in the art will appreciate that mutants useful to the invention may include the zinc finger region of the protein but are not exclusive to the zinc finger region of the protein (see, Natoli et al. *J. Biol. Chem.* (1998) 273:31262-31272). The mutants may be identified by introducing specific desired mutations into a particular region of the A20 gene and testing the resultant mutant protein for a desired activity.

In vitro, A20 has a dual "cytoprotective" role in EC because it is both anti-apoptotic and anti-inflammatory. In vivo, A20 is expressed in EC and SMC of long term surviving hamster to rat heart xenografts and is associated with the absence of inflammation, apoptosis, and of TAV in long term surviving hamster to rat xenograft (Bach et al., *Nature Medicine* (1997) 3:196-204). It has been demonstrated that the anti-inflammatory effect of A20 is mediated via blockade of the transcription factor NF-κB (see Grilli et al., *International Review of Cytology*, (1993) 13:1-61).

A20 Function in SMC and EC

NF-κB is a transcriptional activator associated with immediate early gene expression in EC activation. NF-κB is usually sequestered in the cytoplasm in association with its inhibitor IκBα (Baldwin, *Ann. Rev. Immunol.* (1996) 14:649-681). Upon exposure to stimuli such as lipopolysaccharide (LPS), TNF, or oxygen radicals, IκBα is phosphorylated, ubiquitinated and subsequently degraded in the proteasome allowing translocation of NF-κB to the nucleus of the EC (Traenckner et al., *EMBO J.* (1994) 13:5433-5441; Traenckner et al., *J. Cell Sci. Suppl.* (1995) 19:79-84). In the nucleus, the binding of NF-κB to certain NF-κB binding sites (kB elements) in promoter regions of the nuclear DNA initiates transcription of genes directly or indirectly under the control of these promoters. This leads to de novo expression in EC of a number of NF-κB-dependent genes including adhesion molecules, chemokines, and pro-thrombotic factors that are the hallmarks of the inflammatory phenotype (Read et al., *J. Exp. Med.* (1994) 179:503-512; Bach et al., *Immunological Reviews*, (1994) 141:5-30; Collins, *Lab. Invest.* (1993) 68:499-508). EC activation promotes inflammation and can lead to apoptosis of these cells.

Prior to the present invention, evidence from EC suggested that A20 belongs to a sub-set of TNF-inducible genes which assist in ultimately conferring resistance to TNF-induced apoptosis in EC (see, Tewari et al., *J. Immunol.* (1995) 1699-1706; Ferran et al., *Blood* (1998) 91:2249-2258; Opipari et al., *J. Biol. Chem.* (1990) 285: 14705-14708; Dixit et al., *J. Biol. Chem.* (1990) 264, 16905-16909). It was shown that TNF induces expression of A20 in EC, through NF-κB binding sites located in the A20 promoter, extending from −45 to −54 (5'-GGAAATCCCC-3') (SEQ ID NO:3) and from −57 to −66 (5'-GGAAAGTCCC-3') (SEQ ID NO:4) of the A20 gene (Laherty et al., *J. Biol. Chem.* (1993,) 268, 5032-5039; Krikos et. al., *J. Biol. Chem.* (1992) 267:17971-17976).

The proliferation of SMC, like EC, requires activation of the transcription factor NF-κB, as demonstrated in vitro and in atherosclerotic plaques in vivo (Brand et al., *J. Clin. Invest.* (1996) 97:1715-1722; Bourcier et al., *J. Biol. Chem.* (1997) 272:15817-15824; Bellas et al., *J. Clin. Invest.* (1995) 96:2521-2527). Activation of SMC provides a critical patho-physiological basis for a variety of conditions, including allo- and xenograft rejection, vasculitis, as well as atherosclerosis and TAV. Inflammatory cytokines, CD40-CD40L cognate interactions, oxidized lipids, oxidative stress, as well as growth factors present in both human atheroma and chronic transplant vasculopathy can activate NF-κB and elicit specific functions in SMC (Obata et al., *Biochem. Bioph. Res. Com.* (1996) 224:27-32; Mach et al., *Proc. Natl. Acad. Sci USA* (1997) 94:1931-1936).

The mode of activation of SMC proliferation via NF-κB remains unclear. However, without limiting the biochemical mechanism of the invention, we propose that NF-κB may drive the cell cycle through induction of cyclin D1, in the mid-G1 phase of the cell cycle (Hinz et al., *Mol. Cell. Biol.* (1999) 19:2690-2698; Sherr et al., *Cell.* (1993) 73:1059-1065; Roberts, *Cell.* (1999) 98:129-132). Inhibition of the cell cycle in SMC inhibits SMC proliferation and has been demonstrated to redirect the vascular disease response away from neointimal hyperplasia and toward medial hypertrophy (Mann et al., *Proc. Natl. Acad. Sci. USA* (1995) 92:4502-4506; Chang et al., *Science* (1995) 267:518-522; Kato et al., *Exp. Mol. Pathol.* (1999) 66:39-52; Yang et al., *Proc. Natl. Acad. Sci. USA* (1996) 93:7905-7910). In addition to its anti-proliferative effect, blockade of NF-κB would also serve an anti-inflammatory function by inhibiting the up-regulation of NF-κB dependent genes that are deleterious for the development of atherosclerosis (e.g., adhesion molecules ICAM-1 and VCAM-1, pro-inflammatory receptors CD40 and CD40L, growth factors, and matrix proteinases) (Ross et a., supra; Ardehali et al., supra; Mach et al., *Nature* (1998) 394:200-203).

Clinical trials aimed at blocking a single growth or inflammatory factor have failed to show efficacy. We concluded that this is not surprising given the redundancy of the system via the multiplicity of growth factors and pro-inflammatory mediators that contribute to the pathogenesis of atherosclerosis. We proposed that a more successful approach may be to target the components of intracellular signaling cascades that are shared in response to many of these growth regulatory molecules and pro-inflammatory stimuli. We reasoned that if A20 inhibits NF-κB activation in SMC, as it does in EC, A20 expression could be instrumental in inhibiting SMC proliferation and protecting vascular tissues and organs from atherosclerosis and TAV.

Thus, A20 provides a critical pathophysiological basis of a variety of conditions, including allo- and xenograft rejection, vasculitis and atherosclerosis. U.S. Ser. No. 08/601,515, filed Feb. 14, 1996, abandoned, incorporated herein by reference, discloses the use of gene therapy techniques utilizing A20 and other anti-apoptotic/anti-inflanunatory genes and their expression products to prevent and treat inflammation in endothelial cells.

We further hypothesized that if A20 inhibits NF-κB activation in SMC as it does in EC, A20 expression could block SMC proliferation and prevent or reduce atherosclerosis and TAV. Without limiting the biochemical mechanism of the invention, we proposed that the underlying mechanism of atherosclerosis and TAV is NF-κB stimulation of SMC proliferation. Surprisingly, upon testing this hypothesis, we found that A20, typically thought to act as an anti-apoptotic factor, acts as a pro-apoptotic factor in SMC.

Therapeutic Strategies

The present invention provides therapeutic strategies directed at up-regulating pro-apoptotic factors (or down-regulating anti-apoptotic factors) for inhibition of vascular lesion formation and prevention or treatment of vascular disease. Preferably, the protective gene should achieve an anti-proliferative and pro-apoptotic effect in SMC. According to the present invention, protection of SMCs in the vessel wall that appear to underlie the development of lesions associated with atherosclerosis, TAV, and other vascular diseases can be achieved by modifying the SMC so that it expresses a pro-apoptotic factor.

We demonstrate herein that A20 is expressed in SMC in response to TNF (a pro-inflammatory stimulus), establishing that A20 expression as part of the physiological response of SMC to injury (see, Example 1). In addition, we show that overexpression of A20 in SMC inhibits NF-κB activation in response to TNF (see, Example 1). This NF-κB blockade in SMC correlates with suppression of NF-κB-dependent pro-inflammatory gene expression (e.g., ICAM-1) and SMC proliferation, both of which are involved in the development of atherosclerosis.

As noted above, we also discovered that expression of A20, to date viewed as an anti-apoptotic gene, sensitizes SMC to cytokine-mediated apoptosis, a surprising finding. This novel function of A20 in SMC further augments its anti-atherogenic potential by combining anti-proliferative and pro-apoptotic functions. Interestingly, SMC seem very resistant to apoptotic stimuli in vitro, including nitric oxide, oxidized LDL, high levels of cytokines (IFN-γ, TNF-α an IL-1β), anti-oxidants such as PDTC, Fas-mediated apoptosis, and growth factor deprivation (Geng, et al., *Arterioscler. Thromb. Vasc. Biol.* (1996) 16:19-27; Tsai et al., *J. Biol. Chem.* (1996) 271:3667-3670; Björkerud et al., *Arterioscler. Thromb. Vasc. Biol.* (1996) 16:415-424; Pollman et al., *Circ. Res.* (1996) 79:748-756; Fox et al., *J. Biol. Chem.* (1996) 271:12578-12584). Furthermore, we found that sensitization of SMC to apoptosis by expressing A20 is more potent than for cells expressing IκBα (the specific inhibitor of NF-κB), suggesting that A20 has targets in SMC other than NF-κB.

The present invention establishes that modification of SMC to express A20 may protect vessels and vascularized organs from atherosclerosis and TAV. The results described herein combined with our finding that A20 is expressed in SMC of long term surviving hamster to rat heart xenografts lacking transplant arteriosclerosis (Bach et al., supra) lend support to this proposal. Thus, the present invention sets the basis for the use of A20 and other pro-apoptotic factors as gene therapy tools in pre-clinical and clinical protocols. This approach has immediate clinical potential in vascular conditions.

The present invention provides a method of treating vascular disease by (1) modifying a smooth muscle cell by inserting into the smooth muscle cell a therapeutic gene that achieves an anti-inflammatory, pro-apoptotic, effect in smooth muscle cells, and (2) transplanting the smooth muscle cell, or tissue, or organ comprising the smooth muscle cell into a patient diagnosed with a vascular disease or a transplant candidate (i.e., a patient having end-stage organ failure).

Alternatively, the method of the invention can be used to prevent vascular disease, for example TAV, by (1) modifying a smooth muscle cell by inserting into the smooth muscle cell a therapeutic gene that achieves an anti-inflammatory, pro-apoptotic effect in smooth muscles cells, and (2) transplanting the smooth muscle cell, or tissue, or organ comprising the smooth muscle cell into a patient at risk for developing TAV. Patients at risk for developing TAV include patients receiving allo- or xenogeneic tissue or organ transplants. For example, a patient scheduled to receive a heart transplant would be classified as a patient at risk for developing TAV.

According to the present invention, a therapeutic gene is a DNA sequence encoding a protein capable of decreasing inflammation (e.g., by inhibiting NF-κB activation in a smooth muscle cell) and increasing apoptosis in a smooth muscle cell, thus acting as a dual/anti-inflammatory, pro-apoptotic factor. In preferred embodiments, the therapeutic gene also achieves an anti-proliferative effect in smooth muscle cells. Most preferably, the therapeutic gene further achieves an anti-inflammatory effect in endothelial cells in addition to smooth muscle cells. The therapeutic gene A20 has been demonstrated to have anti-inflammatory, anti-proliferative, and pro-apoptotic activities in smooth muscle cells and also retains an anti-inflammatory effect in EC. Thus, according to a most preferred embodiment of the invention, A20 is the therapeutic gene used in the present invention. Alternatively, the present invention utilizes a therapeutic gene encoding a mutant or derivative of the A20 protein.

In a related aspect, the invention comprises a method of treating a dysfunctional activation response of a smooth muscle cell to an inflammatory or other activation stimulus, by inserting into the smooth muscle cell, DNA encoding a polypeptide having the pro-apoptotic activity of an A20 protein in operative association with a suitable promoter and expressing the polypeptide at effective levels, whereby apoptosis in the smooth muscle cell is substantially activated. The DNA sequence including the pro-apoptotic protein or polypeptide may also include, for example, a transcriptional termination region and an appropriate signal sequence, e.g., a mitochondrial specific signal sequence to provide site-specific targeting ability to the pro-apoptotic factor.

The promoter and/or the protein encoding region of the present invention may be heterologous (i.e., non-native) to the cell. Alternatively, one or both of the protein encoding region and the promoter region may be native to the cell. The promoter may be a promoter other than the promoter which normally controls expression of the pro-apoptotic factor (e.g., A20) in the cell. Preferably the promoter controlling the expression of the protein encoding region is a constitutive, regulable, and/or tissue specific promoter. One feature of a regulable promoter is that it may be inducible, that is, transcription (and thus protein expression) can be activated on demand in response to a stimulus. An advantage of employing an inducible promoter for transplantation purposes is that the desired high level expression of the pro-apoptotic protein or polypeptide (e.g., A20) can be obtained on demand in response to a predetermined stimulus, such as e.g., the presence of tetracycline in the cellular environment. An example of a tetracycline-inducible promoter which is suitable for use in the invention is disclosed by Furth et al., (*PNAS USA* (1994) 91:9302-9306). A regulable promoter system in which transcription is initiated by the withdrawal of tetracycline is described by Gossen and Bujard, (*PNAS USA* (1992) 90:5547-51).

Preferably, expression of the anti-inflammatory/pro-apoptotic protein or polypeptide is induced in response to a predetermined external stimulus, and the stimulus is applied immediately prior to subjecting the SMC to an activating stimulus, so that expression, for example, of A20, is already at effective levels to block NF-κB activation and thereby inhibit inflammation and promote apoptosis. Preferably, the anti-inflammatory/pro-apoptotic protein or polypeptide is also expressed at a level sufficient to block smooth muscle cell proliferation. The activities of blocking inflammation and proliferation are clearly anti-atherogenic.

It is preferred that the invention also includes the smooth muscle cells, modified as described above, and tissues or organs comprising smooth muscle cells. Accordingly, the invention provides a smooth muscle cell modified to express A20, or a mutant or derivative of A20. In preferred embodiments, the A20 protein is capable of inhibiting inflammation and promoting apoptosis in the presence of a cellular activating stimulus. As a result, the modified smooth muscle cell exhibits increased apoptosis relative to an untreated smooth muscle cell. Preferably, the A20 protein is also capable of blocking smooth muscle cell proliferation. Accordingly, the present invention further provides a donor smooth muscle cell, or a tissue, or organ having the donor smooth muscle cell, for transplantation into a recipient species, wherein the donor cell is modified to express A20.

In yet another related aspect, the present invention provides an organ or vessel from a non-human transgenic or somatic recombinant mammal containing DNA encoding a pro-apoptotic protein of a different species. Preferably, the non-human organ or vessel is a porcine organ or vessel that has been modified to express a pro-apoptotic factor. The pro-apoptotic factor is preferably human, for example human A20.

Such cells, tissues and organs as described above can be used in surgical procedures such as heart, liver, or kidney transplantation. Additionally, a modified vessel according to the present invention, can be used, for example, as a vascularized organ transplant and in vascular surgery.

In a related aspect, the present invention provides a method of preparing a vascularized organ or vessel for transplantation into a patient including (1) obtaining an organ or vessel for transplant; and (2) perfusing the organ with nucleic acid encoding A20 protein, or mutants or derivatives thereof. Preferably, the prepared organ or vessel is a vascularized organ or a vascular graft. The prepared vascularized organ or vessel can then be used, for example, in a transplantation procedure to treat a patient that has suffered ischemia, reperfusion injury, mechanical injury, immunologic injury, pharmacologic injury, coronary trauma or other vascular disease. Alternatively, the modified vascularized organ or vessel can be used in a patient who has undergone balloon angioplasty. Most preferably, the modified vascularized organ or vessel is used to replace a diseased vascularized organ or vessel.

For example, cells of a donor mammal (e.g., porcine) may be modified according to the invention by insertion of a pro-apoptotic gene (e.g., porcine or human) under the control of a promoter which is inducible by a drug such as, for example, tetracycline. The animal, whether a somatic recombinant or a transgenic, may be raised to the desired level of maturity under tetracycline-free conditions, until such time as the cells, or tissue, or organs comprising the cells, are to be surgically removed for transplantation purposes. In such case, prior to surgical removal of the organ, the donor animal may be administered tetracycline in order to begin inducing high levels of expression of the anti-apoptotic protein. The organ can then be transplanted into a recipient (e.g., human), and tetracycline may continue to be administered to the recipient for a sufficient time to maintain the protein at the desired levels in the transplanted cells to inhibit NF-κB activation.

Alternatively, after being surgically removed from the donor, the organ can be maintained ex vivo in a tetracycline-containing medium until such time as grafting into a recipient is appropriate.

Preferably, the inserted DNA sequences are incorporated into the genome of the cell. Alternatively, the inserted DNA sequences may be maintained in the cell extrachromosomally, either stably or for a limited period.

The modification of smooth muscle cells or endothelial cells, according to the invention, may be carried out in vivo or ex vivo. Thus, in one aspect, the invention provides a method for substantially promoting apoptosis and substantially inhibiting inflammation in smooth muscle cells by applying an activation stimulus in vivo, to a patient in need of such therapy. The method includes modifying smooth muscle cells of a patient in vivo by inserting into the smooth muscle cells, DNA encoding a pro-apoptotic protein in operative association with a constitutive or inducible promoter and expressing the protein at effective levels, whereby NF-κB activation is also substantially inhibited.

Nucleic acid molecules are provided in solution or in any other pharmacologically suitable form for administration. Conveniently, the subject compositions are administered intravascularly, particularly intraarterially. The target neointimal lesion may be subject to isolation, so as to limit the flow of blood or allow for an extended period of incubation. For example, the blood vessels of an organ (e.g., a kidney) can be temporarily clamped off from the blood circulation of the patient, and the vessels perfused with a solution comprising a transmissible vector construct containing the subject pro-apoptotic gene, for a time sufficient for at least some cells of the organ to be modified by insertion therein of the vector construct. Upon removal of the clamps, blood flow can then be restored to the organ and its normal functioning resumed. Alternatively, the active agents may be maintained in the region by virtue of having a specific affinity for target cells (perhaps via a targeting molecule), or may be allowed to flow through the vasculature. The time of incubation sufficient to deliver the nucleic acids to the cells of the vasculature is usually less than about one hour, more usually less than about 30 minutes, but may be for any period of time that is both effective and practical for the in vivo isolated segment of blood vessel.

There are many delivery methods known in the art for enhancing the uptake of nucleic acids by cells. Useful delivery systems include the Sendai virus-liposome delivery systems (see Rapaport and Shai (1994) *J. Biol. Chem.* 269:15124-15131), cationic liposomes, polymeric delivery gels or matrices, porous balloon catheters (Shi et al. (1994) *Circulation* 90:955-951; and Shi et al. (1994) *Gene Therapy* 1:408-414), intraluminal pressure (PCT/US96/06271, herein incorporated by reference), retrovirus expression vectors, and the like.

The use of liposomes as delivery vehicles is one particular method of interest. The liposomes fuse with the cells of the target site and deliver their contents intracellularly. As noted above, liposomes are maintained in contact with the cells for a time sufficient for fusion, using various means to maintain contact, such as isolation, binding agents, and the like. Liposomes may be prepared with purified proteins or peptides that mediate fusion of membranes, such as those of the Sendai virus or influenza virus, etc. The lipids may be any useful combination of known liposome forming lipids, including, for example, cationic lipids, such as phosphatidylcholine. The remaining lipid will normally be neutral lipids, such as cholesterol, phosphatidyl serine, phosphatidyl glycerol, and the like.

Liposomes may be prepared by the procedure described by Kato et al. (*J. Biol. Chem.* (1991) 266:3361). This method allows for the incorporation into the lumen, high molecular weight molecules, particularly nucleic acids of one kilobase pair or more. In this way oligonucleotides, plasmids, large genes, chromosomal fragments, viruses or viral segments may be introduced into cells efficiently.

In another aspect, cell populations can be removed from the patient or donor animal, modified ex vivo by insertion of vector DNA, and re-implanted into the patient or transplanted into another recipient. For example, an organ can be removed from a patient or donor and subjected to the perfusion step described above ex vivo. Following perfusion with the gene construct, the organ can be re-grafted into the patient or implanted into a different recipient of the same or different species.

Gene transfer could also be performed in allografts or xenografts using ex vivo transduction of the organ prior to transplantation. For xenotransplantation, transgenesis could be planned and is a well known technique in the field (see below). If successful, such an approach could be applied to all vascularized organs, especially the heart where allograft vasculopathy has emerged as the leading cause of death among transplant recipients after the first year.

For gene delivery, a variety of vectors or plasmids are available (see, Maniatis et al. (1989) Molecular Cloning: A Laboratory Manual, Cold Spring Harbor, N.Y.; Ausubel et al., Current Protocols in Molecular Biology, Greene Publishing Associates, New York, V. 1&2 1996; Harlow and Lane Antibodies, A Laboratory Manual, Cold Spring Harbor Laboratory, 1988, incorporated by reference herein). The common vectors described herein are able to transiently or stably be maintained in smooth muscle cells, usually for a period of at least about one day, more usually for a period of at least about several days.

Retroviral vectors (particularly lentivirus vectors, which can infect non-replicating cells), and replication-defective retroviral vectors lacking one or more of the gag, pol, and env sequences required for retroviral replication, are well-known to the art and may be used to transform endothelial or other mammalian cells. PA 317 cells or other producer cell lines producing helper-free viral vectors are well-described in the literature. A representative retroviral construct comprises at least one viral long terminal repeat and promoter sequence upstream of the nucleotide sequence of the therapeutic substance and at least one viral long terminal repeat and polyadenylation signal downstream of the sequence.

Vectors derived from adenoviruses, i.e. viruses that cause upper respiratory disease in humans and are present in latent infections in primates, are also generally known in the art and are particularly preferred for use in the present invention. The ability of adenoviruses to attach to cells at low ambient temperatures is an advantage in the transplant setting which can facilitate gene transfer during cold preservation of tissues or organs. Adenoviral mediated gene transfer into vessels or organs by means of transduction perfusion is also a means of modifying cells in vivo. (Guzman et al. *Circulation* (1993) 88:2838-2848; Lemarchand, *Circulation Res.* (1993) 72:1132-1138) Accordingly, the method of the present invention further provides a method of preventing or treating vascular disease, for example, atherosclerosis and TAV, by transplanting donor smooth muscle cells, or graftable tissues or organs that are composed of smooth muscle cells, to a mammalian recipient having vascular disease or end-stage organ disease (i.e., any transplant candidate) by (1) modifying the donor smooth muscle cells, or progenitors cells thereof, by inserting into the smooth muscle cell, DNA encoding the A20 protein or mutant or derivative thereof; and (2) transplanting the resultant modified donor cells, or tissues or organs having such modified cells, into the recipient so that A20 is expressed in the transplanted cells, thereby substantially promoting apoptosis.

The donor species may be any species which is the same or different from the recipient species, and which is able to provide the appropriate cells, tissues, or organs for transplantation into the recipient species. The donor may be of a species which is allogeneic or xenogeneic to that of the recipient. Preferably, the recipient is a mammal, e.g., a primate. Most preferably the recipient is human. For human recipients, it is envisaged that human (i.e. allogeneic) as well as pig (i.e. xenogeneic) donors will be suitable, but any other mammalian species (e.g., bovine or non-human primate) may also be suitable as donors. For example, porcine aortic smooth muscle cells, or the progenitor cells thereof, can be modified to express porcine or human A20 protein at effective levels for grafting into a human recipient.

Heterologous DNA encoding the A20 or another pro-apoptotic protein can be inserted into the animal or an ancestor of the animal at the single-cell stage or early morula stage. The preferred stage is the single-cell stage although the process may be carried out between the two and eight cell stages. A transgenic animal can thereby be obtained, which will pass the heterologous DNA on to its offspring.

Methods of preparing transgenic pigs are included in Example 4. Methods of preparing transgenic pigs are well known in the art, as discussed by Pinckert et al., *Xeno*, Vol. 2, No. 1, 1994 and the references cited therein, incorporated by reference herein. Of course, any transgenic animal may be used in the present invention. Pigs are particularly preferred because they are particularly amenable for xenotransplantation into a human recipient. Preferably, the xenotransplanted tissue is in the form of an organ, for example, kidney, heart, or liver. Transgenic pigs may be produced by homologous recombination and other such techniques that destroy wild-type gene function. By way of example, transgenic pigs may be produced utilizing homologous recombination techniques to produce a transgenic animal expressing the A20 protein, preferably the human A20 protein.

In another aspect, nucleic acid encoding the preferred genes can be inserted into somatic/body cells of the donor animal to provide a somatic recombinant animal from which the DNA construct is not capable of being passed on to offspring (see, e.g., Miller, A. D. and Rosman, G. T., *Biotechniques* (1989) 7(9):980-990). Appropriate well-known methods of inserting foreign cells or DNA into animal tissue include, for example, micro-injection, embryonic stem cell manipulation, electroporation, cell gun, transduction, transfection, retroviral infection, adenoviruses, etc.

Prior to implantation into a recipient species, the treated smooth muscle cells, tissue or organ may be screened for modified cells containing and expressing the construct. For this purpose, the vector construct can also be provided with a second nucleotide sequence encoding an expression product that confers resistance to a selectable marker substance. Suitable selection markers for screening include the neo gene, conferring resistance to neomycin or the neomycin analog, G418. Alternatively, a sequence encoding a tag, such as green fluorescent protein (GFP) or hemaglutinin A (HA), may be attached coding region of the A20 protein. Such tags are currently available and in use in our laboratory. Although any mammalian cell can be targeted for insertion of the anti-apoptotic gene, such as endothelial cells, monocytes, NK cells, lymphocytes, or islet cells, the preferred cells for manipulation are smooth muscle cells. The recipient species will primarily be human, but not exclusively. Other mammals, such as non-human primates, may be suitable recipients.

In an alternative embodiment of the invention, the pro-apoptotic polypeptide, or mutant or derivative thereof, may be applied directly to smooth muscle cells, tissues or organs in vivo in a phamaceutically acceptable carrier.

It will be appreciated that the modified donor smooth muscle cells and modified donor tissues and organs described above will be useful in the prevention of xenotransplant rejection (or delayed xenograft rejection or acute vascular xenograft rejection) (see, Bach et al. *Immunology Today* (1996) 17:379-383; Dalmasso et al., *Transplantation* (1991) 52:530-533). Xenotransplant rejection accompanies the transplantation of organs between discordant species and involves an immediate immunologic response of recipient antibodies and the complement system against the transplanted organ.

As described herein, inhibition of xenotransplant rejection may be achieved using the A20 protein of the present invention. This may be accomplished by providing transgenic animals that express the A20 protein of the recipient species. The smooth muscle cells of a donor organ obtained from such an animal can be modified by any one of the gene therapy techniques defined above. Alternatively, a vector containing DNA encoding a protein having pro-apoptotic activity can be introduced into the transgenic animal at the single cell stage or early morula stage. In this way, the resulting transgenic animal will express the complement inhibitory factors and will have smooth muscle cells as defined above. Thus, in a further aspect, the invention also provides smooth muscle cells, tissue, donor organs, and non-human transgenic or somatic recombinant animals, as defined above, which express one or more human complement inhibitory factors.

It will be appreciated by those skilled in the art that the present invention can be applied to prevent or treat a variety of vascular conditions. As described herein, direct adenoviral-mediated transduction of vessels can be used to treat ischemia/reperfusion injuries and post-angioplasty of atherosclerotic plaques of both coronary and peripheral arteries. In addition, as described above, venous grafts may also be modified and used in coronary artery bypass graft surgery or for peripheral re-vascularization of lower extremities (Mann et al., supra).

Identifying Therapeutic Compounds

Compound screening assays maybe used to identify bioactive agents that are capable of inducing A20-mediated apoptosis of smooth muscle cells in vascular lesion cells. Of particular interest are screening assays for agents that induce A20-mediated apoptosis in smooth muscle cells, yet have a low toxicity for other human cells. A wide variety of assays may be used for this purpose, including labeled in vitro protein-protein binding assays, electrophoretic mobility shift assays, immunoassays for protein binding, and the like. Three-dimensional crystal structures prepared from purified protein can be useful for modeling intermolecular interactions, etc.

Accordingly, the present invention further provides a method of identifying compounds that substantially promote apoptosis and substantially inhibit smooth muscle cell growth or proliferation. The method includes the steps of (1) exposing smooth muscle cells to a test compound; and (2) assaying the smooth muscle cells for increased apoptosis and reduced growth or proliferation. For example, one could assay for binding of the test compound compared to A20. Preferably, one could assay for activation of A20 activity. Generally a plurality of assay mixtures are run in parallel with different test compound concentrations to obtain a differential response to the various concentrations. Typically, one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant, and animal extracts are available or readily produced. Additionally, natural or synthetically produced libraries and compounds are readily modified through conventional chemical, physical, and biochemical means, and may be used to produce combinatorial libraries. Known pharmacological agents may be subjected to directed or random chemical modifications, such as acylation, alkylation, esterification, amidification, etc. to produce structural analogs.

The assay of the present invention may be a binding assay, wherein one or more of the molecules may be joined to a label that can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that is detectable in accordance with known procedures.

A variety of other reagents may be included in the binding assay. These include reagents like salts, neutral proteins, e.g. albumin, detergents, etc. that are used to facilitate optimal protein-protein binding and/or reduce nonspecific or background interactions. Reagents that improve the efficiency of the assay, such as protease inhibitors, nuclease inhibitors, anti-microbial agents, etc. may also be used. The mixture of components is added in any order that provides for the requisite binding. Incubations are performed at any suitable temperature, typically between 4° and 40° C. Incubation periods are selected for optimum activity, but may also be optimized to facilitate rapid high-throughput screening. Typically between 0.1 and 1 hours will be sufficient.

Alternatively, the well known yeast double-hybrid system can be used to define new protein-protein interactions (Young, Biol. Reprod, (1998) 58(2):302-311).

Drug Treatment

The present invention further provides a method of treating a patient having a vascularized organ transplant, a vessel transplant, or vascular disease by enhancing A20 biological activity. Once an agent has been identified, as described above, it may be used as a therapeutic agent for vascular disease. Thus, the present discovery can be used to identify other potential therapeutic agents, including novel anti-atherogenic drugs. Alternatively, the present invention provides a method of preventing vascular disease in a patient by enhancing the biological activity of A20. Enhancing A20 biological activity may be accomplished, for example, by administering to the patient a therapeutic agent. The therapeutic agent may be any permeable factor such as a peptide or a protein, for example a cytokine, or a drug, for example, a compound identified in the screening method described above. Alternatively, the activity of A20 may be enhanced by employing a mutant of the wild-type A20 gene that encodes an A20 protein that displays increased biological activity. Measurement of an increase in the biological activity of A20 includes assessing as to whether there is a decrease in inflammation, an increase in apoptosis, or a decrease in proliferation in smooth muscle cells expressing A20 protein (see, Examples).

In other preferred embodiments, the present invention provides a method of promoting apoptosis in smooth muscle cells in a patient by increasing the level of A20 in a patient's smooth muscle cells. Of course, it will be appreciated that one mechanism by which the level of A20 may be increased is by generating smooth muscle cells that express the A20 protein at a higher level than wild-type smooth muscle cells, as described above. Another mechanism includes expressing a derivative or mutant of the A20 gene that encodes an A20 protein that is expressed at a higher level or has increased stability within the smooth muscle cell. Yet another mechanism by which this embodiment is fulfilled is by administering, to a patient, a therapeutic agent, as described above. In the present embodiment, the therapeutic agent may be a transcription factor, for example a transcription factor activated by an inflammatory reaction (e.g., a cytokine) that increases or stabilizes A20 expression in smooth muscle cells. Alternatively, the therapeutic agent may be a compound that induces increased expression or stability of the A20 protein.

One skilled in the art would appreciate that in order to assay for an increased level of A20 in a smooth muscle cell, using either a wild-type A20 protein or a mutant or derivative of A20, one would merely need to compare the quantity of A20 expression in modified and wild-type smooth muscle cells (e.g., by semi-quantitative Western blotting or quantitative PCR). Likewise, one skilled in the art would appreciate that mutants and derivatives of the A20 protein can easily be identified by introducing mutations into the A20 protein and assaying the activity of the A20 protein in smooth muscle cells as described herein. Such an analysis is currently being undertaken.

The compounds having the desired pharmacological activity may be administered, in a physiologically acceptable carrier, to a host for treatment of vascular disease. Depending upon the manner of introduction, the compounds may be provided in a variety of physiologically acceptable carriers and formulations known to one skilled in the art and described, for example, in *Remington's Pharmaceutical Sciences*, (18th edition), ed. A. Gennaro, 1990, Mack Publishing Company, Easton, Pa., incorporated herein by reference. The concentration of the therapeutically active compound in the formulation may vary from about 0.1-100 weight %.

It will be appreciated that the therapeutic agents of the present invention may be coadministered with other agents. For example, the therapeutic agents of the present invention may be coadministered with an immunoregulatory factor (e.g., an immunostimulant, i.e., a cytokine, or an immunosuppressant). Alternatively, a combination of drugs may be administered to a patient to induce a pro-apoptotic effect in smooth muscle cells. Of course, any of the therapeutic agents described herein may be administered along with the A20 protein, or alternatively in conjunction with the overexpression of the A20 protein in a particular organ or tissue.

The therapeutic agents are administered at a dose effective to reduce the dimensions of a pre-existing intimal lesion. Usually the lesion will be reduced in size by at least about 20% over a period of one or more weeks, more usually by at least about 50%, and may be completely regressed.

In an alternative embodiment, the present invention provides a method of treating or preventing vascular disease in a patient by preparing a smooth muscle cell, or tissue or organ comprising a smooth muscle cell, for transplant by treating the smooth muscle cell, or tissue or organ comprising a smooth muscle cell, with a therapeutic agent that increases A20 biological levels, and transplanting the smooth muscle cell, or tissue or organ comprising the smooth muscle cell, treated with said therapeutic agent to a patient at risk for developing vascular disease. In a related embodiment, a therapeutic agent that increases the A20 level in the smooth muscle cells may be used to prepare the smooth muscle cell, or tissue, or organ for transplant.

According to the present invention, the smooth muscle cells, tissues or organs may be prepared in vivo, or ex vivo, as described herein above.

EXAMPLES

The present invention will now be illustrated by the following non-limiting examples. The following example demonstrate the anti-inflammatory/anti-proliferative/pro-apoptotic effect of A20 in smooth muscle cells.

Example 1

A20 Activity in SMC

A20 is Part of the Physiological Response of SMC to TNF

Primary human aortic SMC were cultured in 6 well plates using smooth muscle basal medium (SmBM) (Clonetics, California) supplemented with growth factors, Gentamycin and Amphotericin B. Confluent cells were stimulated with 100 Units of recombinant human (rhu)TNF and RNA was extracted before and at 1 and 6 hours (h) following addition of TNF. RNA samples were analyzed by Northern blot analysis for the expression of A20 using an A20 cDNA probe (Ferran et al., supra). In all experiments, a cDNA probe for human GAPDH was used to evaluate equal loading of RNA. Results showed almost no A20 mRNA expression prior to TNF addition. A20 mRNA was strongly induced 1 h following TNF stimulation and started declining 6 h thereafter (FIG. 1A). The induction of A20 by TNF was confirmed at the protein level by means of immunohistochemistry using a rabbit anti-human A20 polyclonal antibody developed in the laboratory (Ferran et al., supra). A20 protein expression was detected in the cytoplasm of SMC 4 h following TNF treatment (FIG. 1B).

A20 Inhibits NF-κB-Activation in SMC

Vascular SMC, at sites of atherosclerotic lesions and TAV, express features of inflammatory processes, including increased expression of genes encoding growth factors and inducible surface proteins such as adhesion molecules, iNOS, CD40 and CD40L (Bourcier et al., supra; Mach et al., supra; Obrien et al., *Circulation* (1996) 93:672-682). NF-κB has emerged as a regulator of most of these molecules in vascular cells. Inflammatory cytokines, oxidized lipids, activated monocytes, and T cells, all present in both human atheroma and TAV, activate NF-κB and elicit a pro-inflammatory phenotype in SMC. In addition to the pro-inflammatory phenotype, activation of NF-κB is crucial for the acquisition by the SMC of the proliferative phenotype that leads to the formation of a neointima and thus development of arteriosclerotic lesions. We had previously shown that A20 is a broad inhibitor of NF-κB activation in EC (Ferran et al., supra; Cooper et al., *J. Biol. Chem.* (1996) 271:18068-18073). We thus tested whether A20 retains this same function in SMC.

A20 was expressed in human SMC cultures using a recombinant A20 adenovirus (rAd.A20) (kind gift of Dr. V. Dixit). Recombinant Ad.A20 was produced, purified, and titered as described earlier (Ferran et al., supra). In preliminary experiments, different multiplicities of infection (MOI), ranging from 100 to 1,000 plaque forming unit (pfu)/cell, were evaluated. Expression of A20 was tested by means of immunohistochemical analysis. Results show that high expression of A20 is achieved in 95% to 100% of the SMC infected with 500 pfu of rAd.A20/cell without causing any cytotoxicity.

Nuclear and cytoplasmic extracts were prepared, before stimulation with TNF, at 15 minutes following stimulation with TNF, and at 2 h following stimulation with 100U/ml of TNF, from non-infected (non-infected), rAd.A20 or rAd.β-gal-infected SMC. NF-κB activation and binding to specific κB elements were evaluated by means of electrophoretic mobility shift assay (EMSA). A20 expression in SMC inhibited NF-κB binding to DNA (FIG. 2A).

Figure 2B:

We also determined where the signaling pathway leading to NF-κB activation is blocked by A20 in SMC. Cytoplasmic extracts were run on SDS-PAGE 12.5% minigels. IκBα was detected using a rabbit polyclonal IgG antibody (C21 from Santa Cruz) and a peroxidase-conjugated goat anti-rabbit secondary antibody followed by enhanced chemiluminescence detection. A20 expression in SMC inhibited the usual IκBα degradation that occurs 15 minutes following TNF stimulation (FIG. 2B). These results demonstrate that A20 interferes with signaling pathways leading to NF-κB activation at a level upstream of IκBα degradation.

Figure 3:
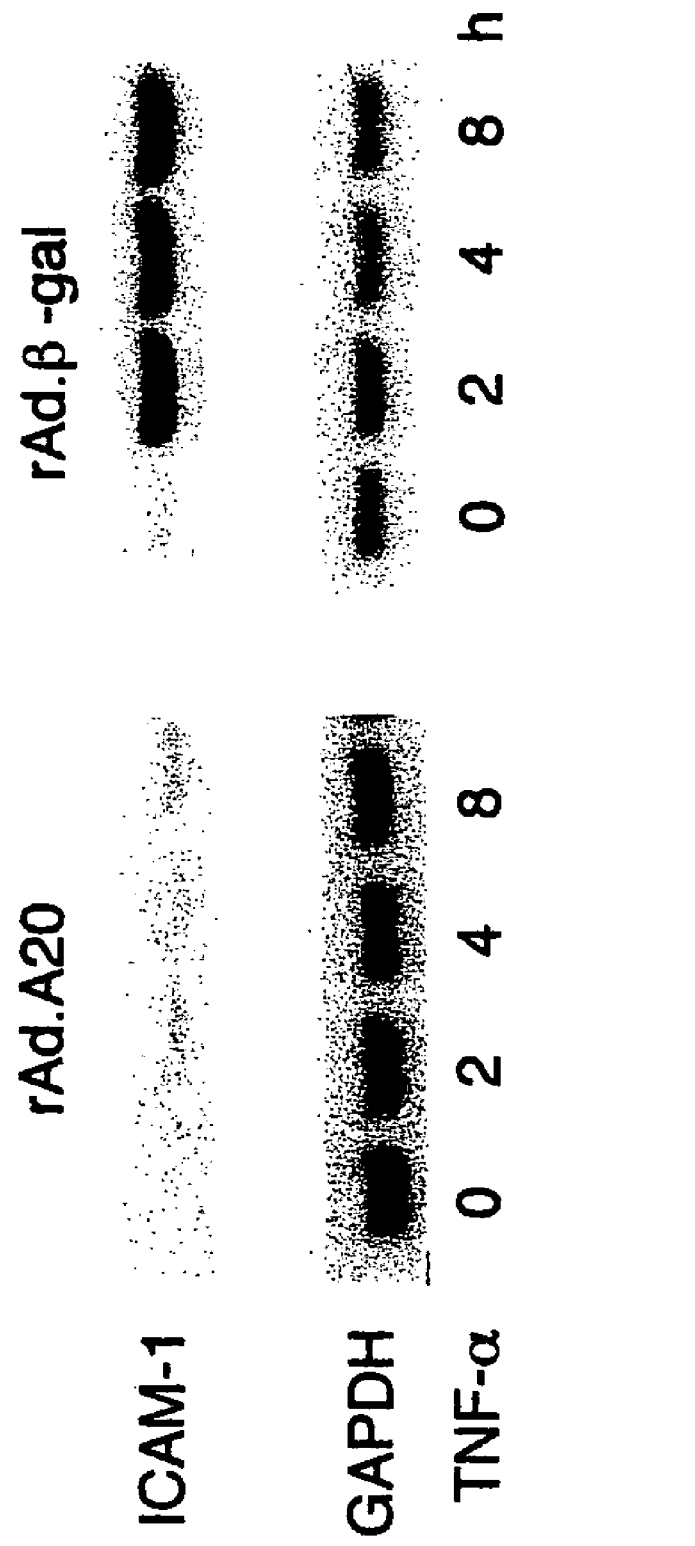
FIG. 3 is a photograph of a Northern blot depicting inhibition of ICAM-1 up-regulation by A20.

Overexpression of A20 Inhibits the Up-Regulation of a NF-κB Dependent Genes in SMC ICAM1 was used as a marker of NF-κB trans-activating potential in SMC. The rationale for using ICAM-1 relies on its role in promoting accumulation of monocytes and lymphocytes that contribute to the development of atherosclerotic lesions. Up-regulation of ICAM-1 following SMC stimulation was evaluated by Northern blot analysis using specific cDNA probes available in the laboratory. Overexpression of A20 inhibited the up-regulation of ICAM-1 mRNA induction in SMC following TNF treatment as compared to non-infected and rAd.β-gal-infected cells (FIG. 3). These results were confirmed at the protein levels.

Figure 7:
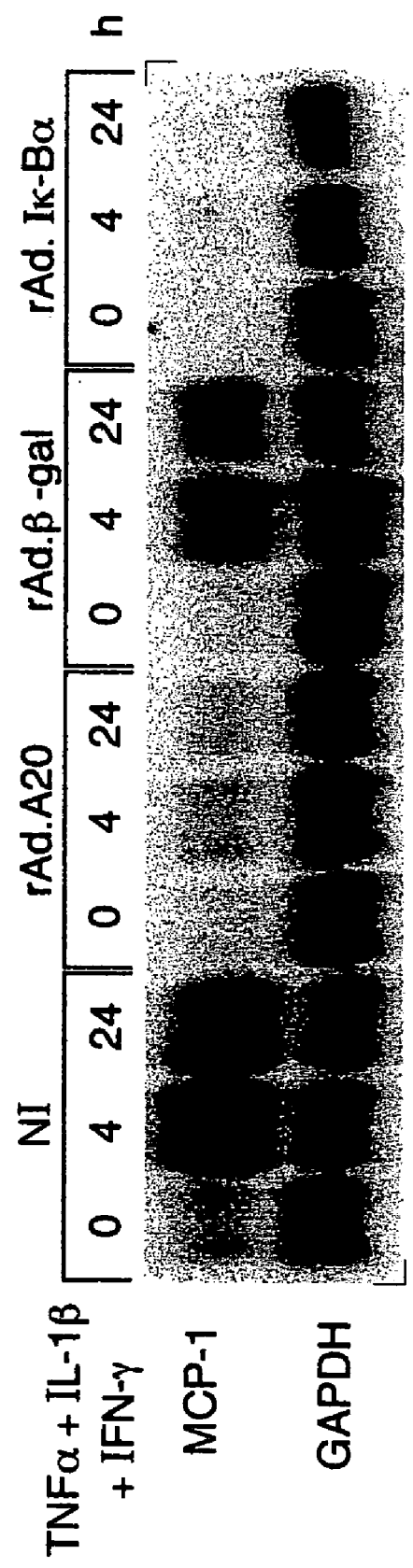
FIG. 7 is a photograph of a Northern blot showing that overexpression of A20 in SMC inhibits TNF-mediated up-regulation of MCP-1 mRNA as compared to not infected (NI) and rAd.β-gal-infected cells.

Another NF-κB dependent gene that has been implicated in the development of atherosclerosis is the chemokine monocyte chemottractant protein (MCP)-1 (Ueda et al., *J. of Immunology* (1994) 153:2052-2063). MCP-1 not only attracts monocytes to the site of vascular inflammation but has also been implicated in promoting SMC migration and proliferation in the neointima (Streblow et al., *Cell* (1999) pages 511-520). Like ICAM-1, induction of MCP-1 by pro-inflammatory cytokines is regulated at the transcription level. Up-regulation of MCP-1 following TNF treatment of SMC was therefore evaluated by Northern blot analysis using a human cDNA probe as described (Millan et al., *Transplantation* (1997) 63:421-429). Over-expression of A20 in SMC inhibited TNF-mediated up-regulation of MCP-1 mRNA as compared to not infected (NI) and rAd.β-gal-infected cells (FIG. 7).

Overexpression of A20 Inhibits SMC Proliferation

Figure 4:
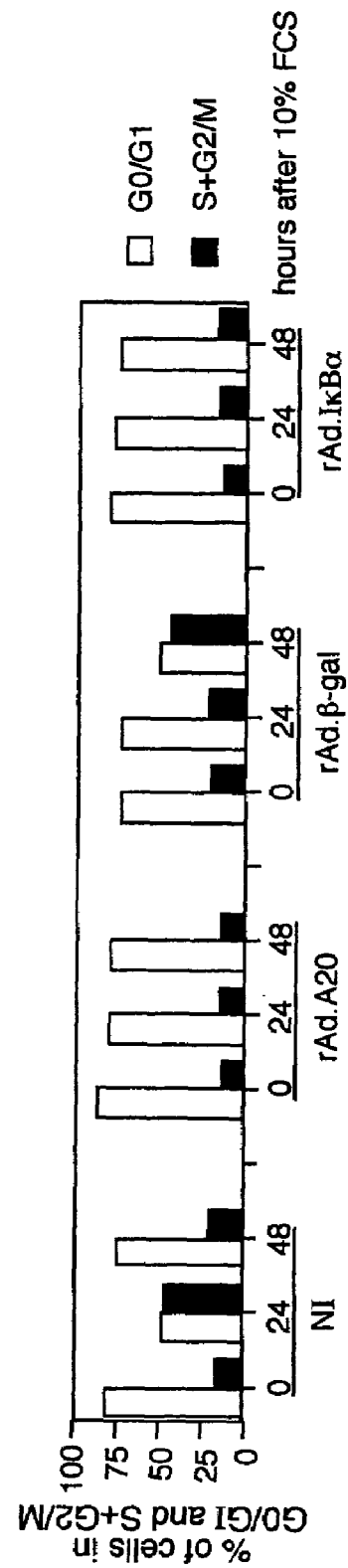
FIG. 4 is a graph depicting inhibition of smooth muscle cell proliferation by A20.

Having established that A20 inhibits NF-κB activation, we tested whether such inhibition would affect the rate of SMC proliferation. Activation of NF-κB has been shown to be essential for SMC proliferation (Selzman et al., *Ann. Thorac. Surg.* (1999) 67:1227-1232). Cultured human SMC were plated at 50 to 60% confluence in 6 well plates and subsequently cultured in 0.5% FCS medium for 48 hours. SMC were kept in the same medium and infected with rAd.A20, rAd. IκBα (kind gift of Dr. Christopher Wrighton), in addition to A20 to achieve NF-κB inhibition, or the control rAd.β-gal. Twenty-four hours following infection, the medium was replaced with 10% FCS and cells were recovered 24 and 48 h later for cell cycle analysis. DNA content was analyzed by FACScan using Cellquest acquisition software. Analysis of DNA ploidy allows discrimination of cells in G0/G1 versus S versus G2/M phases of the cell cycle. Expression of A20 in SMC inhibited progression of the cells through the cell cycle. SMC expressing A20 are blocked in the G0/G1 phase of the cell cycle: 14.4% of the A20 expressing SMC are in the S+G2/M phases of the cell cycle prior to serum addition. This percentage remains essentially the same at 24 and 48 h (16%) following serum addition (FIG. 4). In contrast, non-infected or rAd.β-gal-infected SMC proliferate in response to serum addition and progress to the S+G2/M phases of the cell cycle. The percentage of SMC in S+G2/M phase of the cell cycle before and after serum addition are noted on FIG. 4. SMC expressing the specific inhibitor of NF-κB, IκBα showed a similar pattern of cell cycle inhibition in response to serum as the one obtained in A20 expressing cells. This latter data confirms that of others showing that NF-κB activation is required for SMC proliferation and is blocked by inhibitors of NF-κB (Autieri et al., *Biochem. Bioph. Res. Com.* (1995) 213:827-836; Selzman et al., supra). It also suggests that the inhibitory potential of A20 upon SMC proliferation relates to its ability to block NF-κB activation.

Overexpression of A20 Sensitizes SMC to Cytokine- and Fas-Mediated Apoptosis

Figure 5:
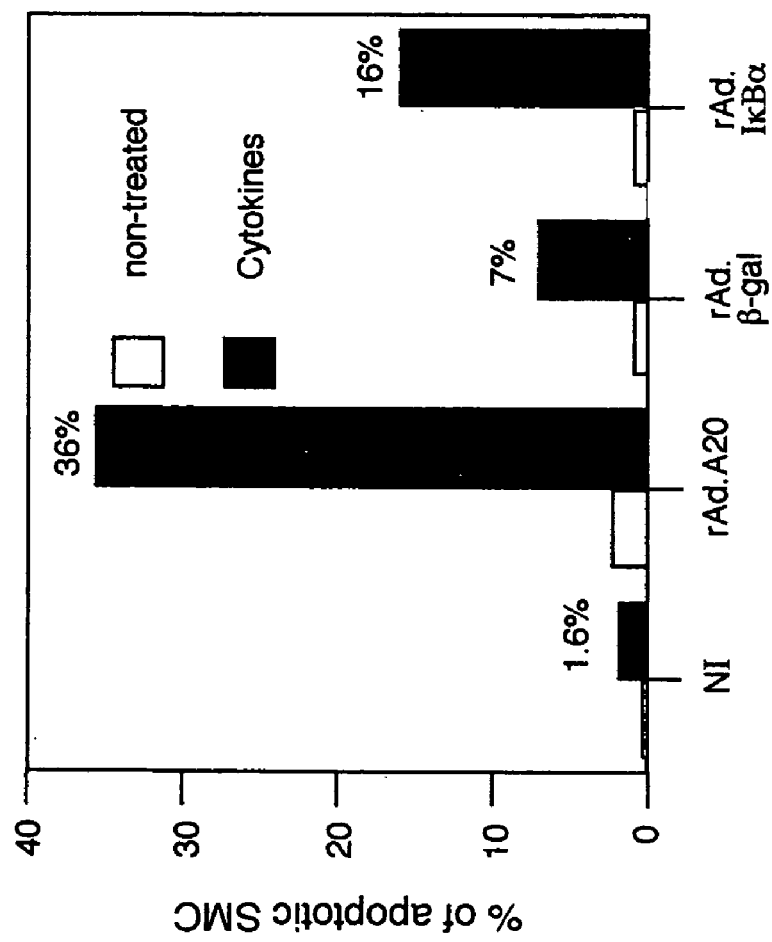
FIG. 5 is a graph depicting A20-induced apoptosis of smooth muscle cells in response to cytokine treatment.

SMC are highly resistant to apoptosis. The molecular basis of this resistance is poorly defined. SMC are readily induced to undergo apoptosis in culture when stimulated with high doses of cytokines including interferon-γ, TNF, and IL-1β, deprived of growth factors, or exposed to oxidized LDL, NO donors or the anti-oxidant pyrrolidine dithiocarbamate (PDTC). We thus tested whether A20, a well accepted anti-apoptotic gene in EC, B cells, and fibroblasts also has this function in SMC. Non-infected, rAd.A20, rAd.β-gal or rAd.IκBα infected SMC were treated with 400 U/ml, of rhuTNF, 400 U/ml rhu IFNγ and 100 U/ml of rhu IL-1β/ml. Forty-eight hours following treatment, cells were harvested, and apoptosis evaluated by DNA content analysis (Ferran et al., supra). Cells with a normal DNA content (>2N) were scored as viable, whereas cells with a hypodiploid DNA content (<2N, termed A0) were scored as apoptotic. Surprisingly, our results revealed that expression of A20 in SMC sensitizes them to cytokine-mediated apoptosis. The percent of apoptotic cells following cytokine treatment increases from 0.3% to 1.6% in non-infected cells, and from 1.2% to 7% in the rAd.β-gal-infected SMC (FIG. 5). In contrast, the percentage of A20-expressing SMC undergoing apoptosis following cytokine treatment increased dramatically and reached 36% at 48 h. Interestingly, expression of IκBα in SMC sensitized the SMC to cytokine-mediated apoptosis, but not to the same extent as A20 despite equivalent inhibition of NF-κB by A20 and IκBα. The percentage of apoptotic SMC expressing IκBα increased from 0.8% to 16% 48 h following cytokine treatment. This data suggests that A20-induced sensitization to cytokine-mediated apoptosis is not solely related to its NF-κB inhibitory activity (FIG. 5).

Figure 8A:
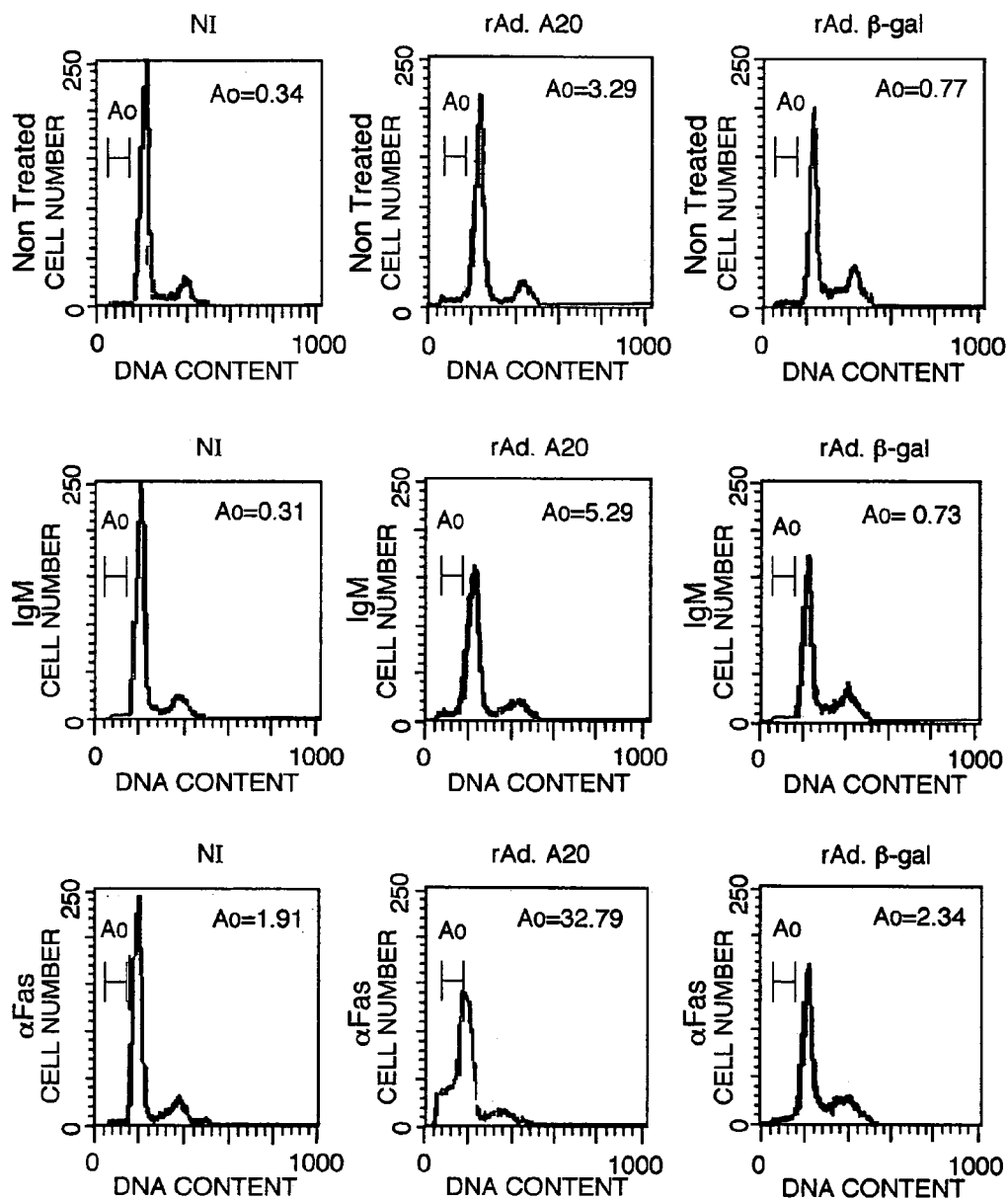
FIG. 8 depicts the percent of not infected (NI), rAd.A20 infected, or rAd.β-gal infected cells undergoing apoptosis in response to various treatments.
Figure 8B:
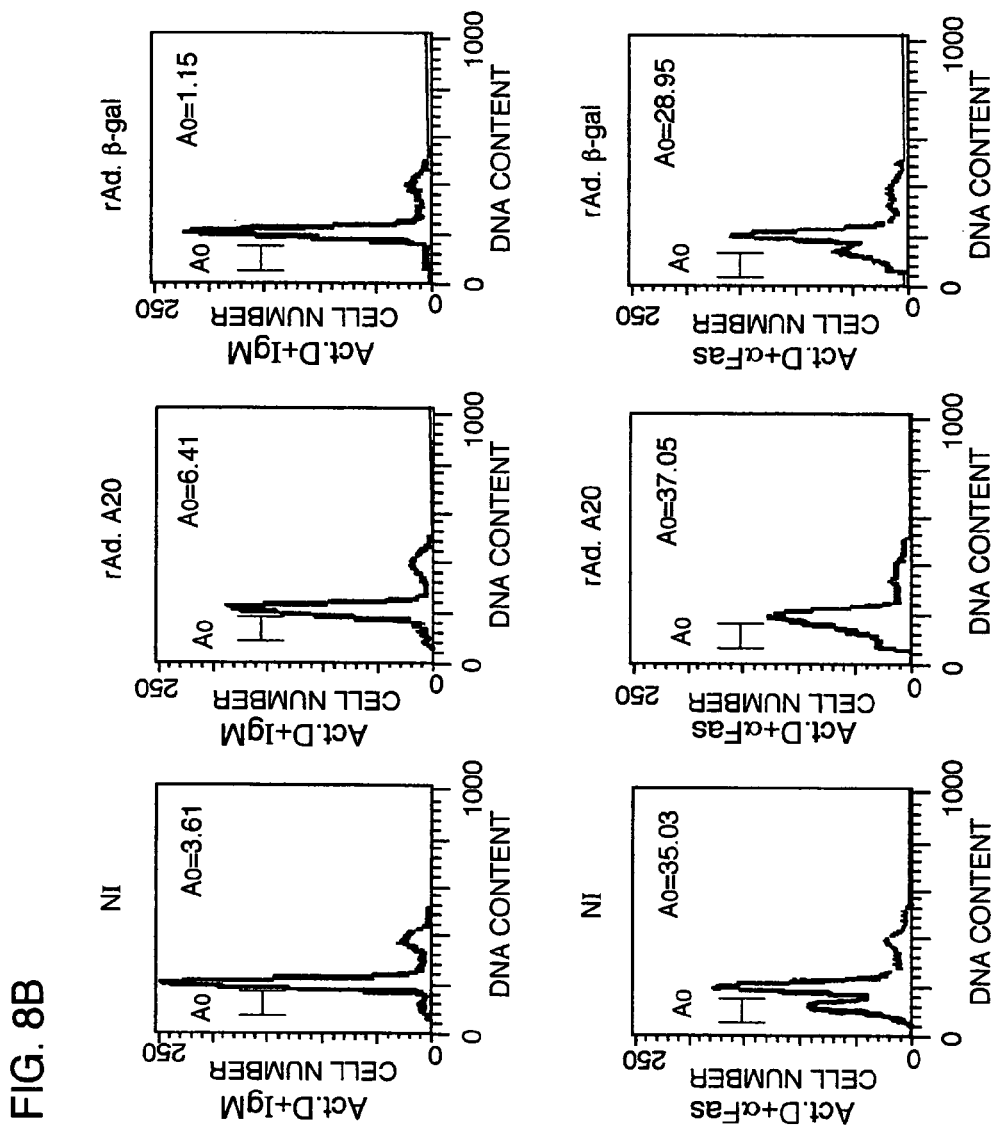

Another apoptotic receptor that is expressed on vascular SMC is Fas (CD95) (Chan et al., *Circ. Res.* (2000) 86:1038-1046). However and despite Fas expression, many cells including SMC resist Fas-induced apoptosis. Interestingly, medial SMC show a marked heterogeneity to Fas-mediated apoptosis with their sensitivity determined not only by surface expression of Fas but also by differential expression of Fas-signaling proteins below receptor level such as caspase 3 (Chan et al., supra). Interestingly, Fas-mediated apoptosis of smooth muscle cells (SMC) has been suggested as a potential means to inhibit neointima formation (Sata et al., *Proc. Natl. Acad. Sci. USA* (1998) 95:11213-1217). Fas ligand gene transfer to the vessels inhibits neointima formation. We thus questioned whether A20-mediated sensitization to cytokine-mediated apoptosis would also apply for Fas-mediated apoptosis. Non-infected, rAd.A20 or rAd.β-gal infected SMC were treated with 1 μg/ml anti-Fas antibody IgM clone CH-11 (αFas) (05-201 Upstate or an IgM control antibody in the presence or absence of Actinomycin D (150 nM). Sixteen hours following treatment, cells were harvested, and apoptosis evaluated by DNA content analysis as described earlier. Cells with a normal DNA content (>2N) were scored as viable, whereas cells with a hypodiploid DNA content (<2N, termed $A_o$) were scored as apoptotic. Our results revealed that expression of A20 in SMC sensitizes them to α-Fas-mediated apoptosis. The percent of apoptotic cells following αFas treatment increases from 0.34% to 1.9% in NI cells, and from 0.7% to 2.34% in the rAd.β-gal-infected SMC (FIG. 8). In contrast, the percentage of A20-expressing SMC undergoing apoptosis following cytokine treatment increased dramatically and reached 33% at 16 hours (FIG. 8). Killing was specific for the αFas antibody as control IgM treatment did not modify the percentage of apoptosis in these cells. Interestingly, pretreatment of EC with Actinomycin D did not significantly modify the percentage of αFas-induced apoptosis in SMC whereas it rendered NI and rAd.β-gal infected SMC more prone to apoptosis with the percentage of apoptotic cells reaching the same level as that in A20 expressing SMC (28-35%) (FIG. 8). These results extend the sensitizing function of A20 to apoptosis in SMC to a clearly relevant stimulus within the atherosclerotic lesion i.e. Fas.

The above-mentioned, rather unexpected, results contrast with the anti-apoptotic function of A20 in EC and other cells. We had previously shown that A20 protects EC from cycloheximide/TNF induced apoptosis and can even overcome IκBα-mediated sensitization of these cells to TNF-induced cell death (Ferran et al., supra).

Expression of A20 in SMC Inhibits αFAS-Mediated Activation of SMC

Figure 9:
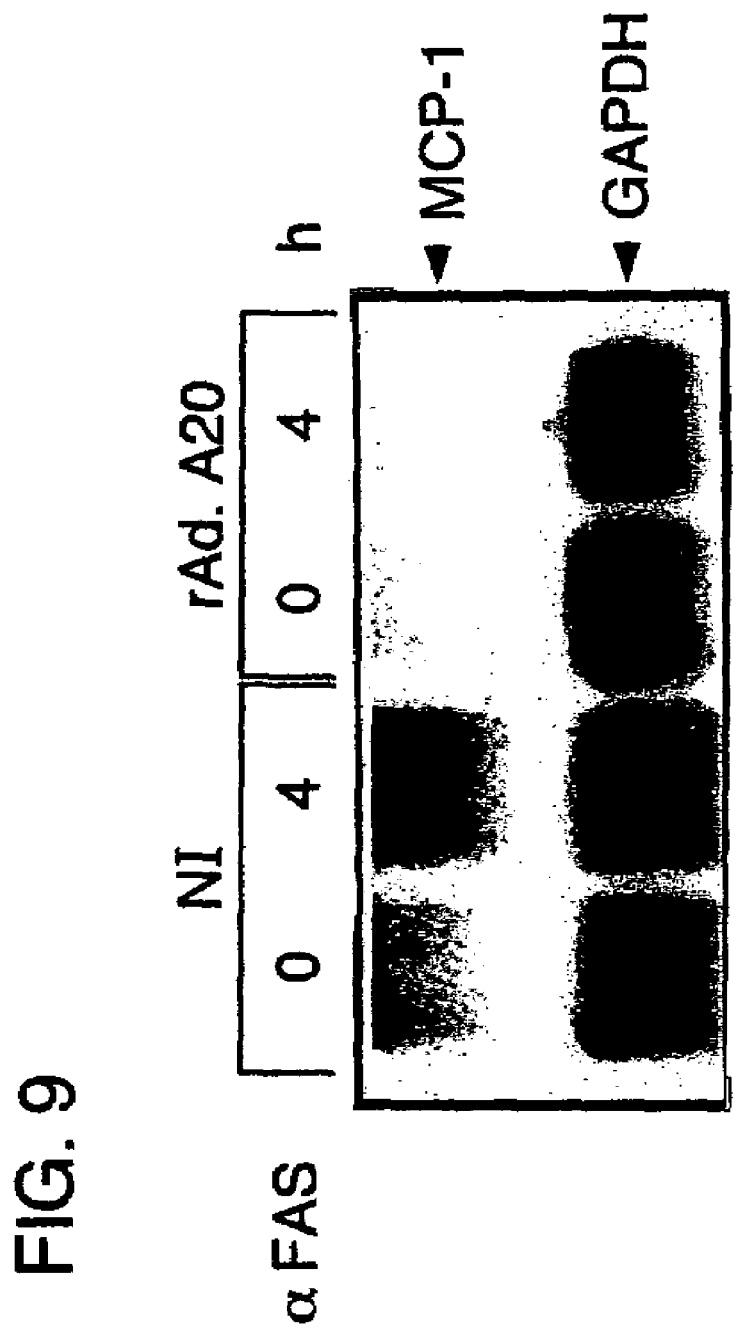
FIG. 9 is a photograph of a Northern blot showing that overexpression of A20 in SMC inhibits αFas-mediated up-regulation of MCP-1 mRNA and also down-regulates the constitutive level detected in not infected (NI) cells.

Having shown that A20 sensitizes SMC to αFas-mediated apoptosis, we were concerned about its impact upon the recently described Fas/FADD-mediated activation of inflammatory gene expression in smooth muscle cells. Indeed, Schaub et al have shown that signals initiated by Fas-associated death domain protein (FADD) in SMC induce the expression of chemokines such as MCP-1 and IL-8 and cause massive immigration of macrophages in vivo at the site of atherosclerotic lesions (Schaub et al., *Nature Medicine* (2000) 6:790-796). These chemokines are also up-regulated during Fas-induced apoptosis in SMC. Induction of a pro-inflammatory program in SMC during Fas-mediated activation and apoptosis could be deleterious and contribute to the pathogenesis of vascular disease, a side-effect that is clearly undesirable if one is aiming to inhibit atherosclerosis. We therefore checked whether expression of A20 in SMC would, as with the cytokines, inhibit Fas-mediated activation of NF-κB and up-regulation of MCP-1. SMC were either NI or infected with rAd.A20. Forty eight hours following infection, SMC were stimulated with 1 μg/ml of αFas antibody and total RNA was extracted at 0 and 4 hours after stimulation. MCP-1 expression following αFas treatment was analyzed by Northern blot analysis using a human MCP-1 probe. Results confirm that MCP-1 mRNA is up-regulated in SMC 4 hours following αFas addition. Overexpression of A20 in SMC inhibited αFas-mediated up-regulation of MCP-1 mRNA and also down-regulated the constitutive level detected in NI cells (FIG. 9).

A20-Mediated Sensitization of SMC to Cytokines is not Associated with a Modification in the Level of the Two Prototypic Anti-Apoptotic BCL Family Members BCL-2 and BCL-$X_L$ Given the sensitizing effect of A20 expression in SMC upon cytokine and Fas-mediated apoptosis, we questioned whether expression of A20 was modifying the level of expression of Bcl-2 and Bcl-$x_L$. SMC were either NI or infected with rAd.A20 and rAd.β-gal as described earlier. Forty eight hours following infection, SMC were stimulated with TNF, IL-1β and IFNγ for 16 hours.

Figure 10:
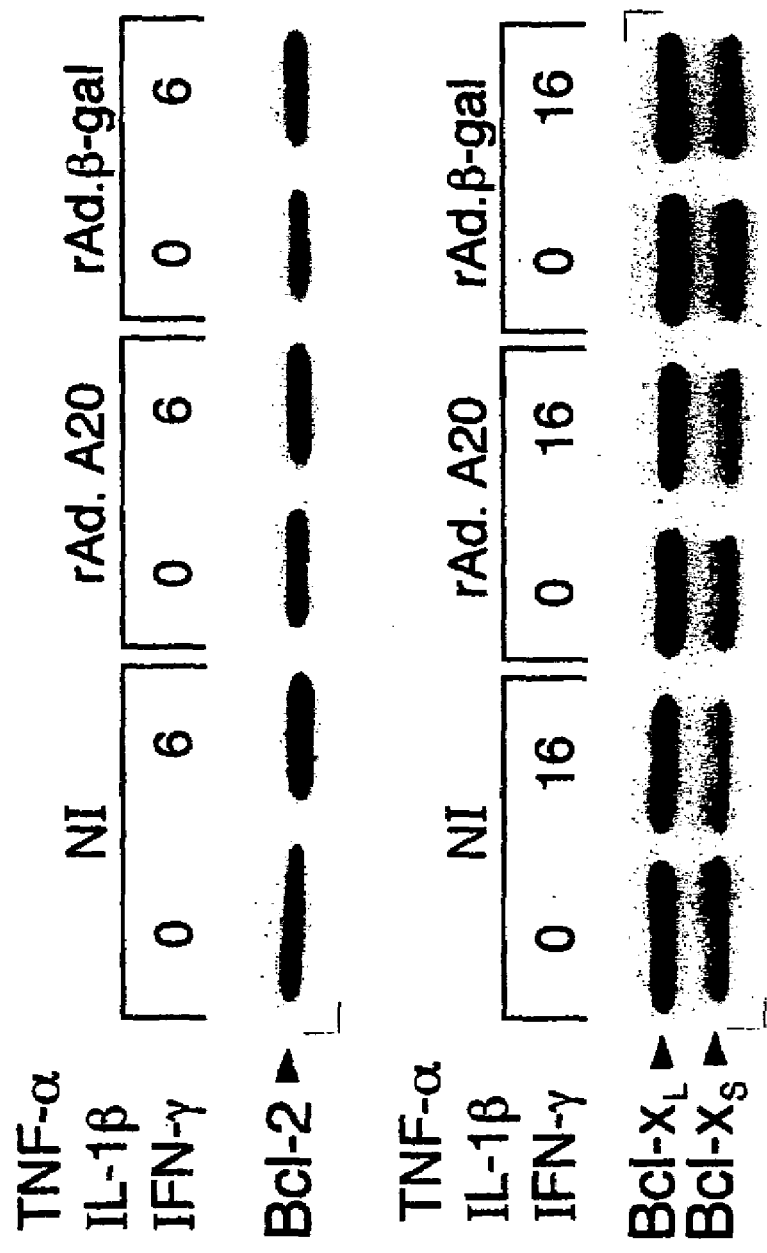
FIG. 10 is a photograph of a Western blot indicating that expression of A20 in SMC does not modify constitutive levels of Bcl-2 or Bcl-$x_L$ expression, nor their levels upon addition of cytokines.

Cells were then trypsinized washed with PBS and subsequently lysed in RIPA Buffer (50 mM Tris pH 7.5, 150 mM NaCl, 1% NP-40, 0.5% Deoxycolate and 1% SDS) supplemented with protease inhibitors (1 μM of aprotinin and leupeptin, 0.1 μM of TLCK and TPCK and 0.5 μM of PMSF). Protein concentration was measured using Bio-RAD $D_c$ protein assay (Bio-Rad, Hercules, Calif.) and fifteen μg of protein were resolved on reducing sodium dodecyl sulfate (SDS) polyacrylamide gels, transferred onto Immobilon-P membranes (Milipore, Bedford, Mass.) and blocked in Blotto (5% non-fat dry milk in 0.1% Tween 20 in PBS). Bcl-$X_{S/L}$ and Bcl-2 were detected using 1/500 dilution of an anti Bcl-$X_{S/L}$ rabbit IgG (Santa Cruz) and a 1/1000 dilution of an anti-Bcl-2 mouse IgG1 mAb (Pharmingen, San Diego, Calif.) followed by a 1/3000 dilution of peroxydase-conjugated donkey anti-rabbit or goat anti-mouse secondary antibody (Pierce, Rockford, Ill.) and revealed by enhanced chemiluminescence (NEN, Boston, Mass.). Results indicate that expression of A20 in SMC does not modify the constitutive levels of expression of Bcl-$x_L$ nor their levels upon addition of cytokines (FIG. 10).

Establishment of a Mouse Line Expressing A20 in EC

Figure 6A:
FIGS. 6A and 6B are photographs of immunohistochemical analysis of A20 expression in heart vessels of control (FIG. 6A) and transgenic (FIG. 6B) mice.
Figure 6B:
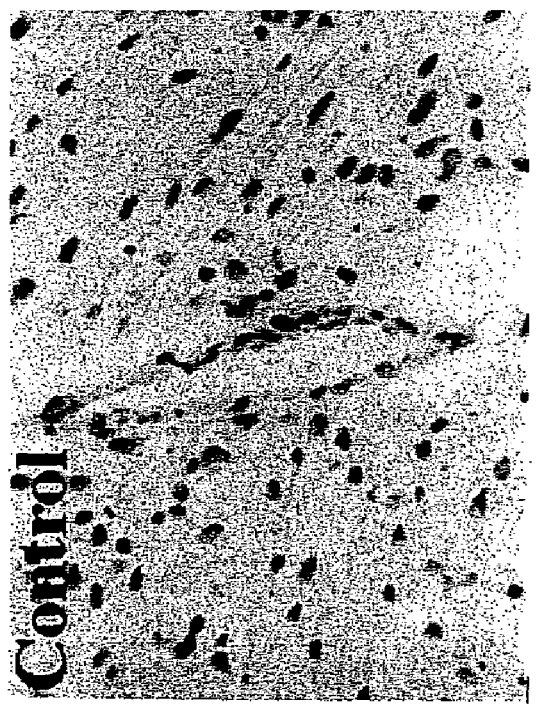

A transgenic mouse line expressing A20 in EC was established using the Complement (C)1 inhibitor promoter that has been shown to induce specific expression of the transgene in EC (Dr. Mario Tozzi, personal communication). Screening for expression of A20 in EC is currently being performed to establish a line of high expressers. Analysis of A20 expression by means of immunohistochemistry shows specific expression of A20 in EC of the heart (FIGS. 6A&B).

Example 2

Evaluation of the Effects of Expressing A20 in SMC In Vitro on Inhibition of NF-κB Activation and the Impact on SMC Activation and Proliferation Induction of A20

One may determine whether A20 expression is part of the physiological response of the SMC to injury.

Fourth to sixth passage human aortic SMC monolayer cultures are activated using different agonists that are relevant to the pathogenesis of atherosclerosis. These agonists include TNF, LDL, and oxidized LDL, growth factors (platelet derived growth factor (PDGF)) and CD40 cross-linking. The expression of A20 in SMC following these agonists is evaluated at different time points (1-24 h), both at the mRNA and protein levels as described in the preliminary results. One then tests whether each of these critical mediators of the atherosclerotic lesion will, like TNF, induce the expression of A20. We propose, without limiting the biochemical mechanism of the invention, that A20 induction is part of the "regulatory" response of SMC to injury. Expression of A20 in the SMC may result in the prevention of neointimal hyperplasia. It is presumably only when these regulatory mechanisms are overwhelmed that atherosclerosis develops.

A20 Overexpression

One may also test the effect of A20 overexpression via adenoviral-mediated gene transfer in SMC upon (i) NF-κB activation, (ii) up-regulation of NF-κB dependent genes such as ICAM1, inducible nitric oxide synthase (iNOS), microphage chemoattractant factor 1 (MCP1) and CD40 (all involved in promoting atherosclerosis) (iii) SMC proliferation and cell cycle regulation. To determine whether the effect of A20 on NF-κB activation is transcription factor specific, one may evaluate whether expression of A20 in SMC affects other transcription factors or signaling pathways involved in SMC proliferation and apoptosis. These include nuclear factor for activated T cells (NF-AT), activated protein-1 (AP-1) and the mitogen-activated protein kinase (MAPK) signaling pathways.

Mechanisms of Action of A20 in SMC Upon NF-κB Activation

The central role of NF-κB activation in the development of atherosclerosis is discussed above. The experiments described here are aimed at confirming and extending, to other pro-atherogenic stimuli, our data showing that overexpression of A20 inhibits TNF-mediated NF-κB activation and NF-κB dependent gene expression in SMC. In addition, one may dissect further the level at which A20 interferes within the signaling pathway leading to NF-κB activation.

SMC cultures overexpressing A20 by means of adenoviral-mediated gene transfer may be activated using oxidized LDL or CD40 cross-linking, two relevant pro-atherogenic stimuli. As discussed above, TNF has already been tested. Whole cells, cytoplasmic and nuclear extracts, and mRNA are harvested at different time points following these treatments and evaluated for (i) expression of the NF-κB dependent genes ICAM-1, VCAM-1, iNOS and CD40, all implicated in the pathogenesis of atherosclerosis; (ii) degradation and phosphorylation of IκBα by means of Western blot analysis; (iii) nuclear translocation of NF-κB by means of EMSA; and (iv) activation of the different kinases (IKKα, IKKβ, NIK and MEKK1) involved in the signaling pathway leading to IκBα phosphorylation (Zandi et al., *Mol. Cell. Biol.* (1999) 19:4547-4551). The effect of A20 on these kinases is tested either by means of specific antibodies recognizing the phosphorylated forms of these kinases or by means of in vitro kinase assay evaluating the activity of these kinases on their specific substrates.

The effect of A20 may also be evaluated on NF-AT and p38 MAP kinase activation to study their potential roles in SMC proliferation and apoptosis (Jing, et al., *Circ. Res.* (1999) 84:831-839; Boss et al., *J. Biol. Chem.* (1998) 273:19664-19671). This study is performed using EMSA and kinase assays. The results obtained with A20 expressing SMC are then compared to those obtained with either non-infected, rAd.β-gal or rAd.IκBα-infected SMC control groups.

We believe that, as in EC, A20 will act in an agonist independent manner as a broad inhibitor of SMC activation and that this inhibition will occur upstream of IκBα degradation and phosphorylation. One may determine the exact level at which A20 interferes within the kinase cascade leading to NF-κB activation and compare these results with our data obtained in EC. A further delineation of a specific target of A20 in SMC provides data valuable to defining novel therapeutic strategies. These data will also determine to what extent the effect of A20 in SMC is specific to NF-κB or affects other transcription factors or signaling pathways relevant for SMC proliferation and apoptosis.

The Effect of A20 Expression Upon SMC Proliferation

SMC proliferation is another marker of NF-κB activation. These experiments test whether by blocking NF-κB activation, A20 will also inhibit SMC proliferation. As described above, SMC cultures are first serum-starved to synchronize their cell cycle within the G0 phase. SMC are then infected with rAd.A20, rAd.IκBα or rAd.β-gal. Entry into the cell cycle and proliferation are then driven by addition of serum or basic fibroblast growth factor (bFGF). Cell cycle progression is then evaluated by means of FACS analysis of DNA content and bromodeoxyuridine incorporation at 24, 48, 60 and 72 h following addition of the growth factors. In addition, cell extracts and mRNA are recovered following the addition of serum to evaluate the effect of A20 expression on cyclin D1, a critical NF-κB-dependent component of the cell cycle. We propose, without limiting the invention, that overexpression of A20 in SMC is likely to be at least as effective as IκBα in inhibiting the proliferation of SMC, with the SMC being retained within the G1 phase of the cell cycle. We believe this effect relates to inhibition of the NF-κB-dependent expression of cyclin D1.

Example 3

A20 Activity In Vivo and In Vitro

Impact of A20 Overexpression upon SMC Apoptosis In Vitro

Apoptosis is now viewed as beneficial to prevent redevelopment and promote the regression of established atherosclerotic lesions. The present invention demonstrates for the first time that A20 sensitizes SMC to cytokine-mediated apoptosis, making A20 a prime gene therapy target to achieve this aim. These experiments are planned to extend our finding that A20 sensitizes SMC to cytokine-mediated apoptosis and to other apoptotic stimuli that are present within the atherosclerotic plaque i.e. Fas, NO and oxidized LDL. Second, one may determine the molecular basis of the effect of A20 upon the death signaling machinery. These studies evaluate the effect of A20 on activation of caspases, mitochondrial membrane potential, c-myc, cytochrome c release and cleavage of death substrates such as PARP that are the hallmarks of apoptosis.

As described above, non-infected SMC and SMC infected with rAd.A20, rAd.IκBα or rAd.β-gal are subjected to 4 different pro-apoptotic stimuli, i.e. a combination of TNF, IL-1 and IFNγ, NO donors, oxidized LDL and Fas cross-linking with anti-Fas antibodies. Apoptosis is assayed at 8, 16, 24 and 48 h following stimulation by means of FACS analysis of DNA content. In addition, cell extracts are recovered at 3, 6, 9, 16 and 24 h to analyze (i) the effect of A20 on the activation of both initiator or class I (caspase 8) and effector or class II (caspase 3,9) caspases using specific calorimetric assays and Western blot analysis, (ii) cytochrome c release in the cytoplasm (iii) c-myc expression and (iv) cleavage of PARP. The effect of A20 on modification of the trans-mitochondrial membrane potential will also be evaluated.

We have demonstrated that although anti-apoptotic in EC and other cells, A20 functions to sensitize SMC to TNF-mediated apoptosis and can thus contain abnormal cell growth and proliferation. This seems especially true in an inflammatory environment (which induces expression of A20) that is encountered in rejecting allografts and in lesions of atherosclerosis.

As noted above, this effect relates to more than A20-mediated inhibition of NF-κB, because the sensitizing effect of A20 upon apoptosis is stronger than the one achieved by IκBα despite a similar blockade of NF-κB activation by A20 and IκBα. Evaluating whether A20 has additional effects on other signaling pathways involved in SMC apoptosis such as p38 MAP kinase will further determine the mechanisms by which A20 sensitizes SMC to apoptosis. This novel function of A20 in SMC may indicate specific molecular partners for A20 in SMC. One may identify such specific molecular partners by using a yeast double-hybrid system using A20 as a bait and a SMC cDNA library. These experiments will allow the identification of new partners for A20, in addition to those already described, i.e., TNF receptor-associated factor (TRAF)-1,2 and 6, 14-3-3 and A20 binding inhibitor of NF-κB (ABIN) (Vincenz et al., *J. Biol. Chem.* (1996) 271:20029-20034; Heynink et al., *FEBS Lett.* (1999) 442: 147-150; Heyninck et al., *J. Cell Biol.* (1999) 145:1471-1482; Yeong-Song et al., *Proc. Natl. Acad. Sci. USA* (1996) 93:6721-6725).

The Anti-atherogenic Potential of A20 In Vivo

Both our in vitro and in vivo data provide a rationale for using A20 to counter the development of atherosclerosis. A20 functions in vitro to inhibit SMC activation and proliferation and sensitizes SMC to cytokine-mediated apoptosis. In vivo, A20 expression in SMC of long term surviving heart xenografts and allografts correlates with the absence of atherosclerosis. We propose that A20 has strong anti-atherogenic potential.

Two different models may be used. First, the well established model of balloon injury of carotid arteries in rabbits (Pollman et al., supra, Guzman et al., *Circulation* (1993) 88:2838-2848). This model enables one to study the effect of adenoviral-mediated gene transfer of A20 to the vessel wall (adenoviral-mediated gene transfer to vessels achieves transient but high levels of transgene expression (Guzman et al., supra)) in protecting from intimal hyperplasia, restenosis and atherosclerosis development when the animal are fed a high cholesterol diet.

Second, one may utilize a transgenic mouse expressing A20 in SMC under the control of one of the newly-developed SMC promoters: the Crp2/SmLim promoter or the smooth muscle heavy chain myosin gene promoter (Madsen et al., *Circ. Res.* (1998) 82:908-917; Yet et al., *J. Biol. Chem.* (1998) 273:10530-10537). Of course, a variety of promoters known in the art are also suitable for use in this experiment. A20 is cloned under the control of these promoters and the mice are screened for the presence of the transgene by Southern blot analysis and for expression in vessels by immunohistochemistry. These mice are then used as organ donors in models of chronic allograft or xenograft rejection (Hancock et al., supra; Bach et al., *Transpl. Proc.* (1997) 29:56-58).

Additionally, these mice may be crossed with mice expressing A20 in EC to test whether expression of A20 is required in both EC and SMC to inhibit TAV. Mice expressing A20 in their SMC or in their SMC and EC are then crossed with already established lines of atherosclerosis prone mice (i.e., the LDL receptor knock out or the ApoE deficient mice), to evaluate whether A20 will protect these animals from the development of atherosclerotic lesions (Breslow, *Science* (1996) 272:685-688). Two transgenic mouse lines that may be used are the LDL-receptor deficient mice available through the Jackson Laboratory and the APO E deficient mice (Plump et al., *Cell* (1992) 71:343-352; Ishibashi et al., *J. Clin. Invest.* (1994) 93:1885-1893). The evaluation of the anatomical lesions and their correlation with the expression of the transgene may be performed by immunohistochemistry.

We predict that gene transfer of A20 to the vessel wall will inhibit intimal proliferation and restenosis in the rabbit balloon injury model. Based upon this, clinical therapies using adenoviral or lentiviral vectors may be developed (Morsy et al., *Proc. Natl. Acad. Sci.* (1998) 95:7866-7871; Amado et al., *Science* (1999) 285:674-676). Generation of mice expressing A20 in SMC may be done to confirm the protective function of A20 when expressed in SMC (and EC) in protecting from TAV. Conditional expression of the transgene under the control of the tetracycline operon may be needed to circumvent these potential results. Such constructs are publicly available (Gossen et al., *Proc. Natl. Acad. Sci. USA* (1992) 89:5547-5551).

Example 4

Preparation of Transgenic Mammals

Recombinant constructs are well known in the art, (see, Maniatis et al. (1989) Molecular Cloning: A Laboratory Manual, Cold Spring Harbor, N.Y.). Methods of producing transgenic mammals using recombinant constructs are well known and include, but not limited to, microinjection, embryonic stem (ES) cell manipulation, electroporation, cell gun, transfection, transduction, retroviral infection, etc. Species of constructs may be introduced individually or in groups of two or more types of constructs.

According to one preferred embodiment of the invention, a transgenic pig may be produced that expresses a SMC specific pro-apoptotic factor (e.g., A20). Briefly, estrus may be synchronized in sexually mature gilts (>7 months of age) by feeding an orally active progestogen (allyl trenbolone, AT: 15 mg/gilt/day) for 12 to 14 days. On the last day of AT feeding all gilts may be given an intramuscular injection (IM) of prostaglandin $F_{2\alpha}$ (Lutalyse: 10 mg/injection) at 0800 and 1600 hours. Twenty-four hours after the last day of AT consumption all donor gilts may be administered a single IM injection of pregnant mare serum gonadotropin (PMSG: 1500 IU). Human chorionic gonadotropin (HCG: 750 IU) may be administered to all donors at 80 hours after PMSG.

Following AT withdrawal, donor and recipient gilts may be checked twice daily for signs of estrus using a mature boar. Donors that exhibit estrus within 36 hours following HCG administration may be bred at 12 and 24 hours after the onset of estrus using artificial and natural (respectively) insemination.

Between 59 and 66 hours after the administration of HCG one- and two-cell ova may be surgically recovered from bred donors using the following procedure. General anesthesia may be induced by administering 0.5 mg of acepromazine/kg of body weight and 1.3 mg ketamine/kg of body weight via a peripheral ear vein. Following anesthetization, the reproductive tract may be exteriorized following a mid-ventral laparotomy. A drawn glass cannula (O.D. 5 mm, length 8 cm) may be inserted into the ostium of the oviduct and anchored to the infundibulum using a single silk (2-0) suture. Ova may be flushed in retrograde fashion by inserting a 20 g needle into the lumen of the oviduct 2 cm anterior to the uterotubal junction. Sterile Dulbecco's phosphate buffered saline (PBS) supplemented with 0.4% bovine serum albumin (BSA) may be infused into the oviduct and flushed toward the glass cannula. The medium may be collected into sterile 17×100 mm polystyrene tubes. Flushings may be transferred to 110×60 mm petri dishes and searched at low power (50×) using a Wild M3 stereomicroscope. All one- and two-cell ova may be washed twice in Brinster's Modified Ova Culture-3 medium (BMOC-3) supplemented with 1.5% BSA and transferred to 50 μl drops of BMOC-3 medium under oil. Ova may be stored at 38° C. under a 90% $N_2$, 5% $O_2$, 5% $CO_2$ atmosphere until microinjection is performed.

One- and two-cell ova may be placed in an Eppendorf tube (15 ova per tube) containing 1 ml HEPES Medium supplemented with 1.5% BSA and centrifuged for 6 minutes at 14000×g in order to visualize pronuclei in one-cell and nuclei in two-cell ova. Ova may then be transferred to a 5-10 μl drop of HEPES medium under oil on a depression slide. Microinjection may be performed using a Laborlux microscope with Nomarski optics and two Leitz micromanipulators and 10-1700 copies of construct DNA (linearized at a concentration of about 1 ng/μl of Tris-EDTA buffer) may be injected into one pronuclei in one-cell ova or both nuclei in two-cell ova.

Microinjected ova may be returned to microdrops of BMOC-3 medium under oil and maintained at 38° C. under a 90% $N_2$, 5% $CO_2$, 5% $O_2$ atmosphere prior to their transfer to suitable recipients. Ova may preferably be transferred within 10 hours of recovery.

Only recipients which exhibit estrus on the same day or 24 hours later than the donors may preferably be utilized for embryo transfer. Recipients may be anesthetized as described earlier. Following exteriorization of one oviduct, at least 30 injected one-and/or two-cell ova and 4-6 control ova may be transferred in the following manner. The tubing from a 21 g×¾ butterfly infusion set may be connected to a 1 cc syringe. The ova and 1-2 mls of BMOC-3 medium may be aspirated into the tubing. The tubing may then be fed through the ostium of the oviduct until the tip reaches the lower third or isthmus of the oviduct. The ova may be subsequently expelled as the tubing is slowly withdrawn.

The exposed portion of the reproductive tract may be bathed in a sterile 10% glycerol-0.9% saline solution and returned to the body cavity. The connective tissue encompassing the linea alba, the fat, and the skin may be sutured as three separate layers. An uninterrupted Halstead stitch may be used to close the linea alba. The fat and skin may be closed using a simple continuous and mattress stitch, respectively. A topical antibacterial agent (e.g. Furazolidone) may then be administered to the incision area.

Recipients may be penned in groups of about four and fed 1.8 kg of a standard 16% crude protein corn-soybean pelleted ration. Beginning on day 18 (day 0=onset of estrus), all recipients may be checked daily for signs of estrus using a mature boar. On day 35, pregnancy detection may be performed using ultrasound. On day 107 of gestation recipients may be transferred to the farrowing suite. In order to ensure attendance at farrowing time, farrowing may be induced by the administration of prostaglandin $F_{2a}$ (10 mg/injection) at 0800 and 1400 hours on day 112 of gestation. In all cases, recipients may be expected to farrow within 34 hours following PGF2a administration.

Twenty-four hours after birth, all piglets may be processed, i.e. ears notched, needle teeth clipped, 1 cc of iron dextran administered, etc. A tail biopsy and blood may also be obtained from each pig.

For additional methods for making transgenic pigs see, Pinckert et al., *Xeno*, Vol. 2, No. 1, 1994, incorporated herein by reference. One skilled in the art would, of course, know how to modify these methods from the exact protocols disclosed herein.

SUMMARY

The results above demonstrate a novel function for A20 in SMC: inhibition of SMC proliferation and sensitization to apoptosis. This later function contrasts with the cytoprotective effect of A20 in EC and makes A20 a unique gene therapy tool to protect the vessels from the development of atherosclerosis. Indeed, the conventional paradigm emphasizes the critical role of EC activation and SMC proliferation as two culprits of atherosclerotic lesion progression. The present invention provides evidence that A20 can function to inhibit both of these deleterious components, in part based on the pro-apoptotic effects of A20 in SMC.

The cellular and molecular biology methods that we intend to use in the experiments described above are well known in the art. This includes experimental models of mouse transplantation. The balloon injury model will be carried out under the guidance of surgeons expert in the technique within the NIH-funded Harvard-Longwood Research Training in Vascular Surgery, with which we are associated.

All references cited herein are hereby incorporated by reference in their entirety.

SEQUENCE LISTING

<160> NUMBER OF SEQ ID NOS: 4

<210> SEQ ID NO 1
<211> LENGTH: 4426
<212> TYPE: DNA
<213> ORGANISM: Homo sapiens

<400> SEQUENCE: 1

```
tgccttgacc aggacttggg actttgcgaa aggatcgcgg ggcccggaga ggtgttggag      60
agcacaatgg ctgaacaagt ccttcctcag gctttgtatt tgagcaatat gcggaaagct     120
gtgaagatac gggagagaac tccagaagac atttttaaac ctactaatgg gatcattcat    180
```

-continued

| | |
|---|---|
| cattttaaaa ccatgcaccg atacacactg gaaatgttca gaacttgcca gttttgtcct | 240 |
| cagtttcggg agatcatcca caaagccctc atcgacagaa acatccaggc caccctggaa | 300 |
| agccagaaga aactcaactg gtgtcgagaa gtccggaagc ttgtggcgct gaaaacgaac | 360 |
| ggtgacggca attgcctcat gcatgccact tctcagtaca tgtggggcgt tcaggacaca | 420 |
| gacttggtac tgaggaaggc gctgttcagc acgctcaagg aaacagacac acgcaacttt | 480 |
| aaattccgct ggcaactgga gtctctcaaa tctcaggaat ttgttgaaac ggggctttgc | 540 |
| tatgatactc ggaactggaa tgatgaatgg gacaatctta tcaaaatggc ttccacagac | 600 |
| acacccatgg cccgaagtgg acttcagtac aactcactgg aagaaataca catatttgtc | 660 |
| ctttgcaaca tcctcagaag gccaatcatt gtcatttcag acaaaatgct aagaagtttg | 720 |
| gaatcaggtt ccaatttcgc cccttttgaaa gtgggtggaa tttacttgcc ctccactgg | 780 |
| cctgcccagg aatgctacag ataccccatt gttctcggct atgacagcca tcattttgta | 840 |
| cccttggtga ccctgaagga cagtgggcct gaaatccgag ctgttccact tgttaacaga | 900 |
| gaccggggaa gatttgaaga cttaaaagtt cacttttga cagatcctga aaatgagatg | 960 |
| aaggagaagc tcttaaaaga gtacttaatg gtgatagaaa tccccgtcca aggctgggac | 1020 |
| catggcacaa ctcatctcat caatgccgca agttggatg aagctaactt accaaaagaa | 1080 |
| atcaatctgg tagatgatta ctttgaactt gttcagcatg agtacaagaa atggcaggaa | 1140 |
| aacagcgagc aggggaggag agaggggcac gcccagaatc ccatggaacc ttccgtgccc | 1200 |
| cagctttctc tcatggatgt aaaatgtgaa acgcccaact gccccttctt catgtctgtg | 1260 |
| aacacccagc ctttatgcca tgagtgctca gagaggcggc aaaagaatca aaacaaactc | 1320 |
| ccaaagctga actccaagcc gggccctgag gggctccctg gcatggcgct cggggcctct | 1380 |
| cggggagaag cctatgagcc cttggcgtgg aaccctgagg agtccactgg ggggcctcat | 1440 |
| tcggccccac cgacagcacc cagccctttt ctgttcagtg agaccactgc catgaagtgc | 1500 |
| aggagccccg gctgcccctt cacactgaat gtgcagcaca acggattttg tgaacgttgc | 1560 |
| cacaacgccc ggcaacttca cgccagccac gccccagacc acacaaggca cttggatccc | 1620 |
| gggaagtgcc aagcctgcct ccaggatgtt accaggacat ttaatgggat ctgcagtact | 1680 |
| tgcttcaaaa ggactacagc agaggcctcc tccagcctca gcaccagcct ccctccttcc | 1740 |
| tgtcaccagc gttccaagtc agatccctcg cggctcgtcc ggagcccctc cccgcattct | 1800 |
| tgccacagag ctggaaacga cgcccctgct ggctgcctgt ctcaagctgc acggactcct | 1860 |
| ggggacagga cggggacgag caagtgcaga aaagccggct gcgtgtattt tgggactcca | 1920 |
| gaaaacaagg gcttttgcac actgtgtttc atcgagtaca gagaaaacaa acattttgct | 1980 |
| gctgcctcag ggaaagtcag tcccacagcg tccaggttcc agaacaccat tccgtgcctg | 2040 |
| gggagggaat gcggcaccct tggaagcacc atgtttgaag gatactgcca gaagtgtttc | 2100 |
| attgaagctc agaatcagag atttcatgag gccaaaagga cagaagagca actgagatcg | 2160 |
| agccagcgca gagatgtgcc tcgaaccaca caaagcacct caaggcccaa gtgcgcccgg | 2220 |
| gcctcctgca gaacatcct ggcctgccgc agcgaggagc tctgcatgga gtgtcagcat | 2280 |
| cccaaccaga ggatgggccc tgggcccac cggggtgagc ctgcccccga agaccccccc | 2340 |
| aagcagcgtt gccgggcccc cgcctgtgat catttttggca atgccaagtg caacggctac | 2400 |
| tgcaacgaat gctttcagtt caagcagatg tatggctaac cggaaacagg tgggtcacct | 2460 |
| cctgcaagaa gtgggcctc gagctgtcag tcatcatggt gctatcctct gaaccccctca | 2520 |
| gctgccactg caacagtggg cttaagggtg tctgagcagg agaggaaaga taagctcttc | 2580 |

-continued

```
gtggtgccca cgatgctcag gtttggtaac ccgggagtgt tcccaggtgg ccttagaaag    2640
caaagcttgt aactggcaag ggatgatgtc agattcagcc caaggttcct cctctcctac    2700
caagcaggag gccaggaact tctttggact tggaaggtgt gcggggactg ccgaggccc     2760 ctgcaccctg cgcatcagga ctgcttcatc gtcttggctg agaaagggaa aagacacaca    2820
agtcgcgtgg gttggagaag ccagagccat tccacctccc ctcccccagc atctctcaga    2880
gatgtgaagc cagatcctca tggcagcgag gccctctgca agaagctcaa ggaagctcag    2940
ggaaaatgga cgtattcaga gagtgtttgt agttcatgtg ttttccctac ctgcccggtt    3000
cctttcctga ggacccggca gaaatgcaga accatccatg gactgtgatt ctgaggctgc    3060
tgagactgaa catgttcaca ttgacagaaa acaagctgc tctttataat atgcacctttt   3120 taaaaaatta gaatatttta ctgggaagac gtgtaactct ttgggttatt actgtcttta    3180
cttctaaaga agttagcttg aactgaggag taaaagtgtg tacatatata atataccctt    3240
acattatgta tgagggattt ttttaaatta tattgaaatg ctgccctaga agtacaatag    3300
gaaggctaaa taataataac ctgttttctg gttgttgttg gggcatgagc ttgtgtatac    3360
actgcttgca taaactcaac cagctgcctt tttaaaggga gctctagtcc ttttgtgta    3420 attcacttta tttattttat tacaaacttc aagattattt aagtgaagat atttcttcag    3480
ctctggggaa aatgccacag tgttctcctg agagaacatc cttgctttga gtcaggctgt    3540
gggcaagttc ctgaccacag ggagtaaatt ggcctctttg atacactttt gcttgcctcc    3600
ccaggaaaga aggaattgca tccaaggtat acatacatat tcatcgatgt ttcgtgcttc    3660
tccttatgaa actccagcta tgtaataaaa aactatactc tgtgttctgt taatgcctct    3720
gagtgtccta cctccttgga gatgagatag ggaaggagca gggatgagac tggcaatggt    3780
cacagggaaa gatgtggcct tttgtgatgg ttttattttc tgttaacact gtgtcctggg    3840
ggggctggga agtcccctgc atcccatggt accctggtat tgggacagca aaagccagta    3900
accatgagta tgaggaaatc tctttctgtt gctggcttac agtttctctg tgtgctttgt    3960
ggttgctgtc atatttgctc tagaagaaaa aaaaaaagg aggggaaatg cattttcccc    4020
agagataaag gctgccattt tgggggtctg tacttatggc ctgaaaatat ttgtgatcca    4080
taactctaca cagcctttac tcatactatt aggcacactt tccccttaga gcccctaag    4140 ttttccccag acgaatcttt ataatttcct ttccaaagat accaaataaa cttcagtgtt    4200
ttcatctaat tctcttaaag ttgatatctt aatatttgt gttgatcatt atttccattc     4260
ttaatgtgaa aaaagtaat tatttatact tattataaaa agtatttgaa atttgcacat    4320
ttaattgtcc ctaatagaaa gccacctatt ctttgttgga tttcttcaag ttttttctaaa   4380 taaatgtaac ttttcacaag agtcaacatt aaaaaataaa ttattt                  4426
```

<210> SEQ ID NO 2
<211> LENGTH: 790
<212> TYPE: PRT
<213> ORGANISM: Homo sapiens

<400> SEQUENCE: 2

```
Met Ala Glu Gln Val Leu Pro Gln Ala Leu Tyr Leu Ser Asn Met Arg
 1               5                  10                  15

Lys Ala Val Lys Ile Arg Glu Arg Thr Pro Glu Asp Ile Phe Lys Pro
             20                  25                  30

Thr Asn Gly Ile Ile His His Phe Lys Thr Met His Arg Tyr Thr Leu
         35                  40                  45
```

-continued

```
Glu Met Phe Arg Thr Cys Gln Phe Cys Pro Gln Phe Arg Glu Ile Ile
 50                  55                  60

His Lys Ala Leu Ile Asp Arg Asn Ile Gln Ala Thr Leu Glu Ser Gln
 65                      70                  75                  80

Lys Lys Leu Asn Trp Cys Arg Glu Val Arg Lys Leu Val Ala Leu Lys
                 85                  90                  95

Thr Asn Gly Asp Gly Asn Cys Leu Met His Ala Thr Ser Gln Tyr Met
            100                 105                 110

Trp Gly Val Gln Asp Thr Asp Leu Val Leu Arg Lys Ala Leu Phe Ser
        115                 120                 125

Thr Leu Lys Glu Thr Asp Thr Arg Asn Phe Lys Phe Arg Trp Gln Leu
    130                 135                 140

Glu Ser Leu Lys Ser Gln Glu Phe Val Glu Thr Gly Leu Cys Tyr Asp
145                 150                 155                 160

Thr Arg Asn Trp Asn Asp Glu Trp Asp Asn Leu Ile Lys Met Ala Ser
                165                 170                 175

Thr Asp Thr Pro Met Ala Arg Ser Gly Leu Gln Tyr Asn Ser Leu Glu
            180                 185                 190

Glu Ile His Ile Phe Val Leu Cys Asn Ile Leu Arg Arg Pro Ile Ile
        195                 200                 205

Val Ile Ser Asp Lys Met Leu Arg Ser Leu Glu Ser Gly Ser Asn Phe
    210                 215                 220

Ala Pro Leu Lys Val Gly Gly Ile Tyr Leu Pro Leu His Trp Pro Ala
225                 230                 235                 240

Gln Glu Cys Tyr Arg Tyr Pro Ile Val Leu Gly Tyr Asp Ser His His
                245                 250                 255

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
        275                 280                 285

His Phe Leu Thr Asp Pro Glu Asn Glu Met Lys Glu Lys Leu Leu Lys
    290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
                325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
        355                 360                 365

Ala Gln Asn Pro Met Glu Pro Ser Val Pro Gln Leu Ser Leu Met Asp
    370                 375                 380

Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
                405                 410                 415

Lys Leu Pro Lys Leu Asn Ser Lys Pro Gly Pro Glu Gly Leu Pro Gly
            420                 425                 430

Met Ala Leu Gly Ala Ser Arg Gly Glu Ala Tyr Glu Pro Leu Ala Trp
        435                 440                 445

Asn Pro Glu Glu Ser Thr Gly Gly Pro His Ser Ala Pro Pro Thr Ala
450                 455                 460
```

```
Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
                485                 490                 495

Arg Cys His Asn Ala Arg Gln Leu His Ala Ser His Ala Pro Asp His
            500                 505                 510

Thr Arg His Leu Asp Pro Gly Lys Cys Gln Ala Cys Leu Gln Asp Val
        515                 520                 525

Thr Arg Thr Phe Asn Gly Ile Cys Ser Thr Cys Phe Lys Arg Thr Thr
    530                 535                 540

Ala Glu Ala Ser Ser Ser Leu Ser Thr Ser Leu Pro Pro Ser Cys His
545                 550                 555                 560

Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
            580                 585                 590

Gln Ala Ala Arg Thr Pro Gly Asp Arg Thr Gly Thr Ser Lys Cys Arg
        595                 600                 605

Lys Ala Gly Cys Val Tyr Phe Gly Thr Pro Glu Asn Lys Gly Phe Cys
    610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655

Cys Leu Gly Arg Glu Cys Gly Thr Leu Gly Ser Thr Met Phe Glu Gly
            660                 665                 670

Tyr Cys Gln Lys Cys Phe Ile Glu Ala Gln Asn Gln Arg Phe His Glu
        675                 680                 685

Ala Lys Arg Thr Glu Glu Gln Leu Arg Ser Ser Gln Arg Arg Asp Val
    690                 695                 700

Pro Arg Thr Thr Gln Ser Thr Ser Arg Pro Lys Cys Ala Arg Ala Ser
705                 710                 715                 720

Cys Lys Asn Ile Leu Ala Cys Arg Ser Glu Glu Leu Cys Met Glu Cys
                725                 730                 735

Gln His Pro Asn Gln Arg Met Gly Pro Gly Ala His Arg Gly Glu Pro
            740                 745                 750

Ala Pro Glu Asp Pro Pro Lys Gln Arg Cys Arg Ala Pro Ala Cys Asp
        755                 760                 765

His Phe Gly Asn Ala Lys Cys Asn Gly Tyr Cys Asn Glu Cys Phe Gln
    770                 775                 780

Phe Lys Gln Met Tyr Gly
785                 790

<210> SEQ ID NO 3
<211> LENGTH: 10
<212> TYPE: DNA
<213> ORGANISM: Homo sapiens

<400> SEQUENCE: 3
ggaaatcccc                                                         10

<210> SEQ ID NO 4
<211> LENGTH: 10
<212> TYPE: DNA
<213> ORGANISM: Homo sapiens
```

-continued

```
<400> SEQUENCE: 4
ggaaagtccc                                                          10
```

What is claimed is:

1. A method of treating, inhibiting, or reducing formation or progression of a vascular lesion caused by aberrant proliferation of neointimal smooth muscle cells in a human patient in need thereof comprising inserting into a neointimal smooth muscle cell in said patient directly at the site of said lesion, or directly at a site where a vascular lesion is likely to develop, a nucleic acid comprising a promoter sequence operably linked to a nucleic acid sequence that encodes a protein comprising a sequence having at least 95% sequence identity to the sequence set forth in SEQ ID NO: 2, wherein said protein is capable of decreasing inflammation or capable of increasing apoptosis of said smooth muscle cell, said inserting being conducted under conditions that result in expression of said protein by said smooth muscle cell, wherein expression of said protein inhibits proliferation of said smooth muscle cell, thereby treating, inhibiting, or reducing formation or progression of said vascular lesion in said patient.

2. A method of inhibiting vascular inflammation in a human patient in need thereof comprising inserting into a neointimal smooth muscle cell in said patient directly at the site of said inflammation a nucleic acid comprising a promoter sequence operably linked to a nucleic acid sequence that encodes a protein comprising a sequence having at least 95% sequence identity to the sequence set forth in SEQ ID NO: 2, wherein said protein is capable of decreasing inflammation at the site of said neointimal smooth muscle cell, said inserting being conducted under conditions that result in expression of said protein by said neointimal smooth muscle cell, wherein expression of said protein inhibits said inflammation in said patient.

3. The method of claim 2, wherein said method inhibits inflammation in the presence of tumor necrosis factor-alpha (TNF).

4. A method of treating or inhibiting development of a vascular disease in a human patient in need thereof, wherein said vascular disease is characterized by intimal hyperplasia or NF-κB activation in a smooth muscle cell, comprising inserting into a neointimal smooth muscle cell in said patient directly at the site of said vascular disease, or directly at a site where vascular disease is likely to develop, a nucleic acid comprising a promoter sequence operably linked to a nucleic acid sequence that encodes a protein comprising a sequence having at least 95% sequence identity to the sequence set forth in SEQ ID NO: 2, wherein said protein is capable of decreasing inflammation or capable of increasing apoptosis of said smooth muscle cell, said inserting being conducted under conditions that result in expression of said protein by said smooth muscle cell, whereby expression of said protein treats or inhibits development of said vascular disease in said patient.

5. The method of claim 2, wherein said protein further blocks smooth muscle cell proliferation or increases apoptosis of said smooth muscle cell.

6. The method of claim 1, wherein said nucleic acid is comprised by an adenovirus vector or a lentivirus vector.

7. The method of claim 2, wherein said nucleic acid is comprised by an adenovirus vector or a lentivirus vector.

8. The method of claim 4, wherein said nucleic acid is comprised by an adenovirus vector or a lentivirus vector.

9. The method of claim 1, where said inserting comprises perfusing an organ or vessel comprising said smooth muscle cell with said nucleic acid.

10. The method of claim 2, where said inserting comprises perfusing an organ or vessel comprising said smooth muscle cell with said nucleic acid.

11. The method of claim 4, where said inserting comprises perfusing an organ or vessel comprising said smooth muscle cell with said nucleic acid.

12. The method of claim 1, wherein said patient has atherosclerosis, transplant-associated vasculopathy, or chronic rejection.

13. The method of claim 2, wherein said patient has atherosclerosis, transplant-associated vasculopathy, or chronic rejection.

14. The method of claim 4, wherein said vascular disease is atherosclerosis, transplant-associated vasculopathy, or chronic rejection.

15. The method of claim 1, wherein said patient has suffered ischemia/reperfusion injury, mechanical injury, immunologic injury, pharmacologic injury, or coronary trauma, or has undergone balloon angioplasty.

16. The method of claim 2, wherein said patient has suffered ischemia/reperfusion injury, mechanical injury, immunologic injury, pharmacologic injury, or coronary trauma, or has undergone balloon angioplasty.

17. The method of claim 4, wherein said patient has suffered ischemia/reperfusion injury, mechanical injury, immunologic injury, pharmacologic injury, or coronary trauma, or has undergone balloon angioplasty.

* * * * *

UNITED STATES PATENT AND TRADEMARK OFFICE
CERTIFICATE OF CORRECTION

PATENT NO. : 7,297,685 B2
APPLICATION NO. : 10/461200
DATED : November 20, 2007
INVENTOR(S) : Ferran et al.

It is certified that error appears in the above-identified patent and that said Letters Patent is hereby corrected as shown below:

On Page 2, Under References Cited, Under OTHER PUBLICATIONS,
Under Dixit et al., "Tumor...," replace "nacrosis" with --necrosis--.

On Page 2, Under References Cited, Under OTHER PUBLICATIONS,
Under Fox et al., replace "snooth" with --smooth--.

On Page 2, Under References Cited, Under OTHER PUBLICATIONS,
Under Geng et al., replace "Viro" with --Vitro--.

On Page 2, Under References Cited, Under OTHER PUBLICATIONS,
Under Heyninck et al., "The zinc...," replace "extpression" with --expression--.

On Page 3, Under References Cited, Under OTHER PUBLICATIONS,
Under Miyatake et al., replace "Accomodated" with --Accommodated--.

On Page 3, Under References Cited, Under OTHER PUBLICATIONS,
Under Oltval et al., replace "programed" with --programmed--.

Column 3, Line 17, replace "undergone undergone" with --undergone--.

Column 6, Line 41, replace "IκBA" with --IκBα--.

Column 10,
Line 14, replace "a., supra;" with --al., supra;--.
Line 36, replace "anti-apoptotic/anti-inflanunatory" with --anti-apoptotic/anti-inflammatory--.

Column 15, Line 40, please make "Accordingly, the method..." the beginning of a new paragraph.

Column 16, Line 58, replace "phamaceutically" with --pharmaceutically--.

Column 17, Line 33, replace "maybe" with --may be--.

Column 20, Line 8, replace "example" with --examples--.

UNITED STATES PATENT AND TRADEMARK OFFICE
CERTIFICATE OF CORRECTION

PATENT NO. : 7,297,685 B2
APPLICATION NO. : 10/461200
DATED : November 20, 2007
INVENTOR(S) : Ferran et al.

It is certified that error appears in the above-identified patent and that said Letters Patent is hereby corrected as shown below:

Column 21, Line 35, replace "chemottractant" with --chemoattractant--.

Column 27, Line 20, replace "Heynink" with --Heyninck--.

Column 29, Under SEQUENCE LISTING, replace
"<160> NUMBER OF SEQ ID NOS: 4" with --<160> NUMBER OF SEQ ID NOS: 6--.

Column 39, Under SEQUENCE LISTING, add the following sequences after Sequence 4
--

```
<210> 5
<211> 21
<212> PRT
<213> Artificial Sequence

<220>
<223> synthetic

<221> VARIANT
<222> 2, 3, 4, 5, 7, 8, 9, 10, 11, 12, 13, 14, 15, 16, 17, 19, 20
<223> Xaa = Any Amino Acid
<400> 5
Cys Xaa Xaa Xaa Xaa Cys Xaa Xaa Xaa Xaa Xaa Xaa Xaa Xaa Xaa
 1               5                  10                  15
Xaa Cys Xaa Xaa Cys
            20

<210> 6
<211> 19
<212> PRT
<213> Artificial Sequence

<220>
<223> synthetic

<221> VARIANT
<222> 2, 3, 5, 6, 7, 8, 9, 10, 11, 12, 13, 14, 15, 17, 18
<223> Xaa = Any Amino Acid
```

UNITED STATES PATENT AND TRADEMARK OFFICE
CERTIFICATE OF CORRECTION

PATENT NO.       : 7,297,685 B2
APPLICATION NO.  : 10/461200
DATED            : November 20, 2007
INVENTOR(S)      : Ferran et al.

It is certified that error appears in the above-identified patent and that said Letters Patent is hereby corrected as shown below:

```
<400> 6
Cys Xaa Xaa Cys Xaa Xaa Xaa Xaa Xaa Xaa Xaa Xaa Xaa Xaa Cys
 1               5                  10                  15
Xaa Xaa Cys
```
--.

Signed and Sealed this

Twenty-ninth Day of December, 2009

David J. Kappos
*Director of the United States Patent and Trademark Office*